US012700813B2

(12) United States Patent
Park et al.

(10) Patent No.: US 12,700,813 B2
(45) Date of Patent: Aug. 4, 2026

(54) HIGHLY SENSITIVE SELF-POWERED PRESSURE SENSOR AND THE USE OF THE SAME

(71) Applicant: Industry-Academic Cooperation Foundation, Yonsei University, Seoul (KR)

(72) Inventors: Jin-Woo Park, Seoul (KR); Soyeon Lee, Seoul (KR)

(73) Assignee: Industry-Academic Cooperation Foundation, Yonsei University, Seoul (KR)

( * ) Notice: Subject to any disclaimer, the term of this patent is extended or adjusted under 35 U.S.C. 154(b) by 200 days.

(21) Appl. No.: 18/475,117

(22) Filed: Sep. 26, 2023

(65) Prior Publication Data

US 2024/0364237 A1 Oct. 31, 2024

(30) Foreign Application Priority Data

Sep. 26, 2022 (KR) ........................ 10-2022-0121816

(51) Int. Cl.
*H02N 1/04* (2006.01)
*A61B 5/024* (2006.01)
(Continued)

(52) U.S. Cl.
CPC ........... *H02N 1/04* (2013.01); *A61B 5/02444* (2013.01); *A61B 5/0245* (2013.01); *A61B 2560/0214* (2013.01); *G01H 17/00* (2013.01)

(58) Field of Classification Search
CPC ..... A61B 5/02444; A61B 5/0245; H02N 1/04
See application file for complete search history.

(56) References Cited

U.S. PATENT DOCUMENTS

| 9,790,928 | B2 * | 10/2017 | Wang | ........................ | H02N 1/04 |
| 11,070,148 | B2 * | 7/2021 | Lin | ........................... | H02N 1/04 |
| 2018/0160911 | A1 * | 6/2018 | Fu | ........................... | H02N 1/04 |

FOREIGN PATENT DOCUMENTS

| KR | 20180009585 | 1/2018 |
| KR | 10-2018-0074888 | 7/2018 |

(Continued)

OTHER PUBLICATIONS

Peng, S. et al.; "Rational Design of Ultrasensitive Pressure Sensors by Tailoring Microscopic Features;" *Adv. Mater. Interfaces* 2018; 5; 8 pages; https://doi.org/10.1002/admi.201800403.

(Continued)

*Primary Examiner* — Eric F Winakur
(74) *Attorney, Agent, or Firm* — Thorpe North & Western, LLP.; David W. Osborne

(57) ABSTRACT

Provided is a self-powered pressure sensor which may show excellent pressure sensitivity by significantly improving transfer efficiency of charges generated by triboelectrification, the sensor including: a first electrode; a first triboelectrification unit positioned on the first electrode; a second triboelectrification unit including a pattern on which a microstructure is repeatedly positioned, the microstructure being reversibly in contact with or separated from the first triboelectrification unit by a physical external force, and having at least one surface in contact with the first triboelectrification unit to induce a change in a contact area; and a second electrode positioned inside the second triboelectrification unit and conformally positioned on a surface of the microstructure, wherein the first electrode and the second electrode are geometrically asymmetric to each other.

16 Claims, 26 Drawing Sheets

(51) Int. Cl.
   *A61B 5/0245*      (2006.01)
   *G01H 17/00*      (2006.01)

(56)            References Cited

FOREIGN PATENT DOCUMENTS

| | | |
|---|---|---|
| KR | 10-2018-0080014 | 7/2018 |
| KR | 10-1958807 | 3/2019 |
| KR | 20200028119 | 3/2020 |
| KR | 20200121449 | 10/2020 |
| KR | 20220128195 | 9/2022 |

OTHER PUBLICATIONS

Symposium CH01—"Frontiers of In Situ Materials Characterization—From New Instrumentation and Method to Imaging Aided Materials Design;" May 9-May 24, 2022; 405 pages.
Symposium SF05—"Autonomous Materials for the Next-Generation of Smart Systems"; 2022 MRS Spring Meeting & Exhibit; May 8-13, 2022 (Honolulu, Hawaii) May 23-25, 2022 (Virtual); 17 pages.
Lee, S. et al.; "Fingerprint-inspired triboelectric nanogenerator with a geometrically asymmetric electrode design for a self-powered dynamic pressure sensor;" Nano Energy; vol. 101; 2022; 107546; ISSN 2211-2855; https://doi.org/10.1016/j.nanoen.2022.107546; 12 pages.

* cited by examiner

[FIG. 1]
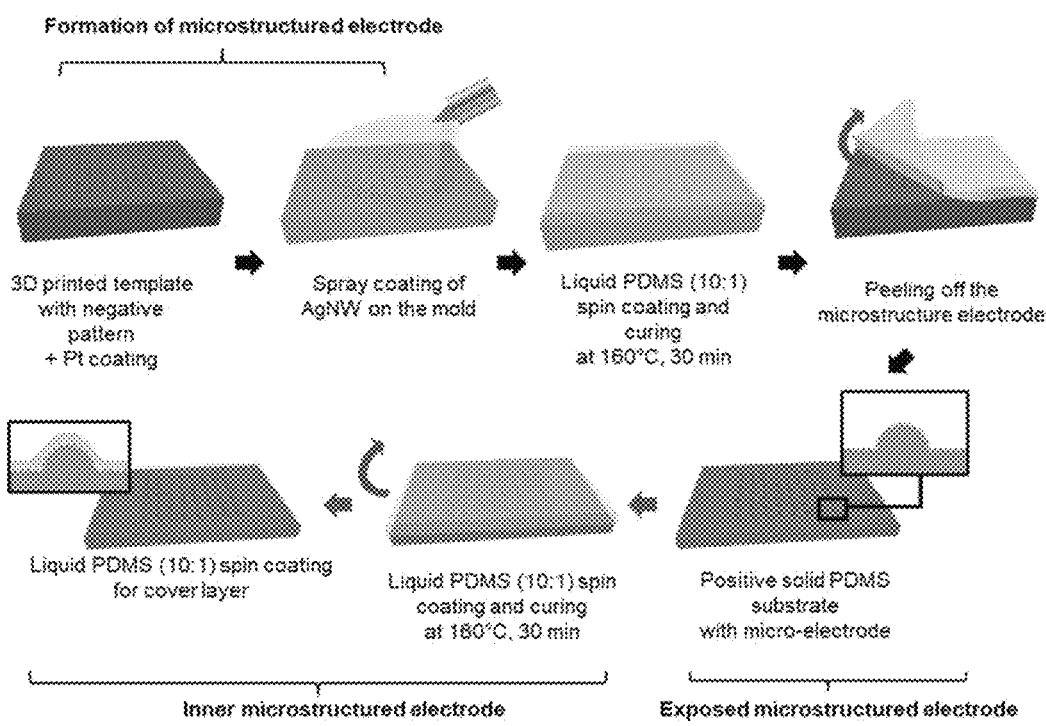

[FIG. 2]
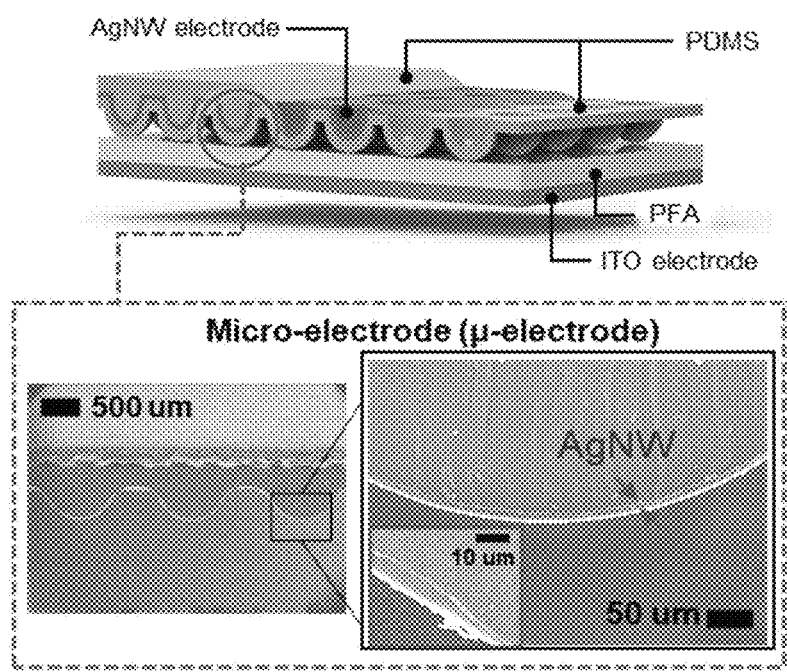

[FIG. 3]
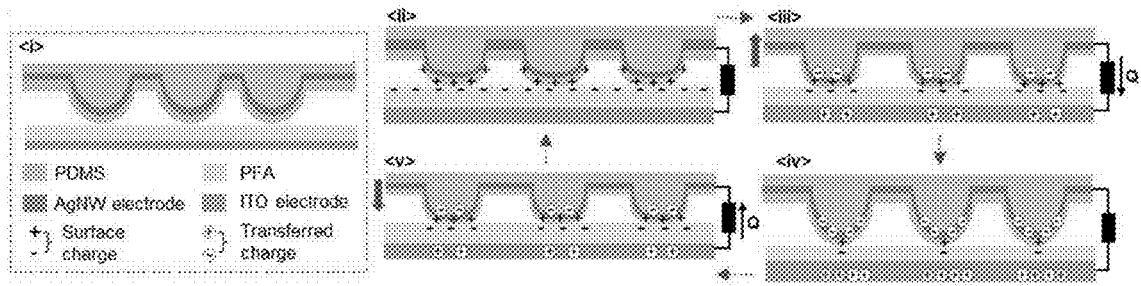

[FIG. 4]
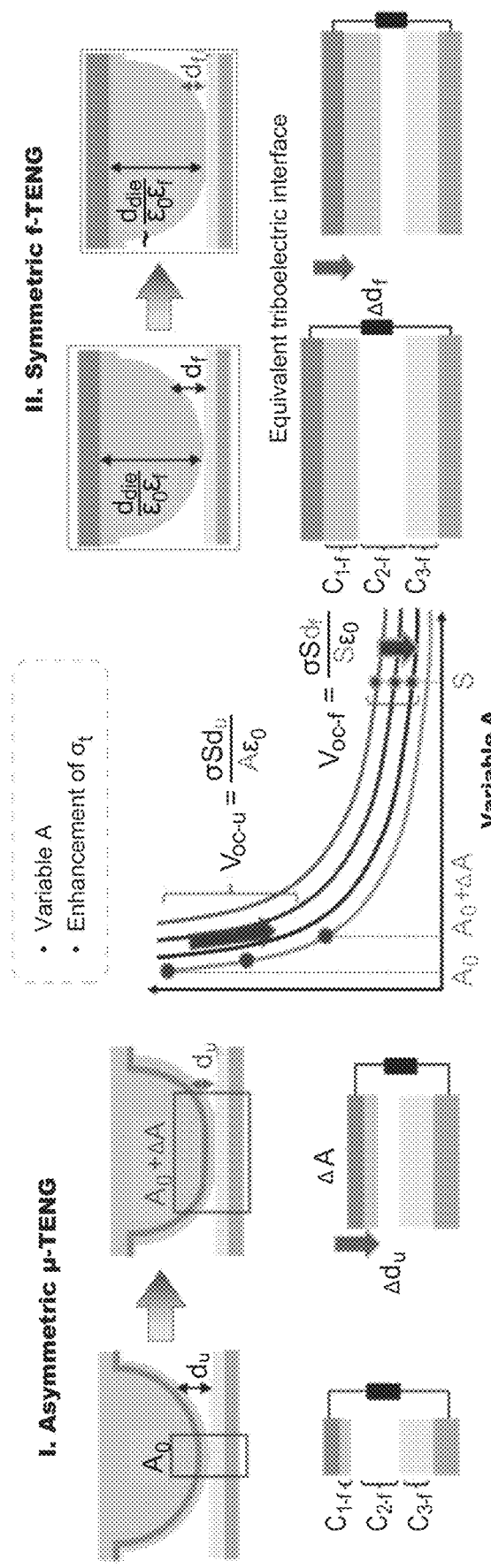

[FIG. 5A]
(a)
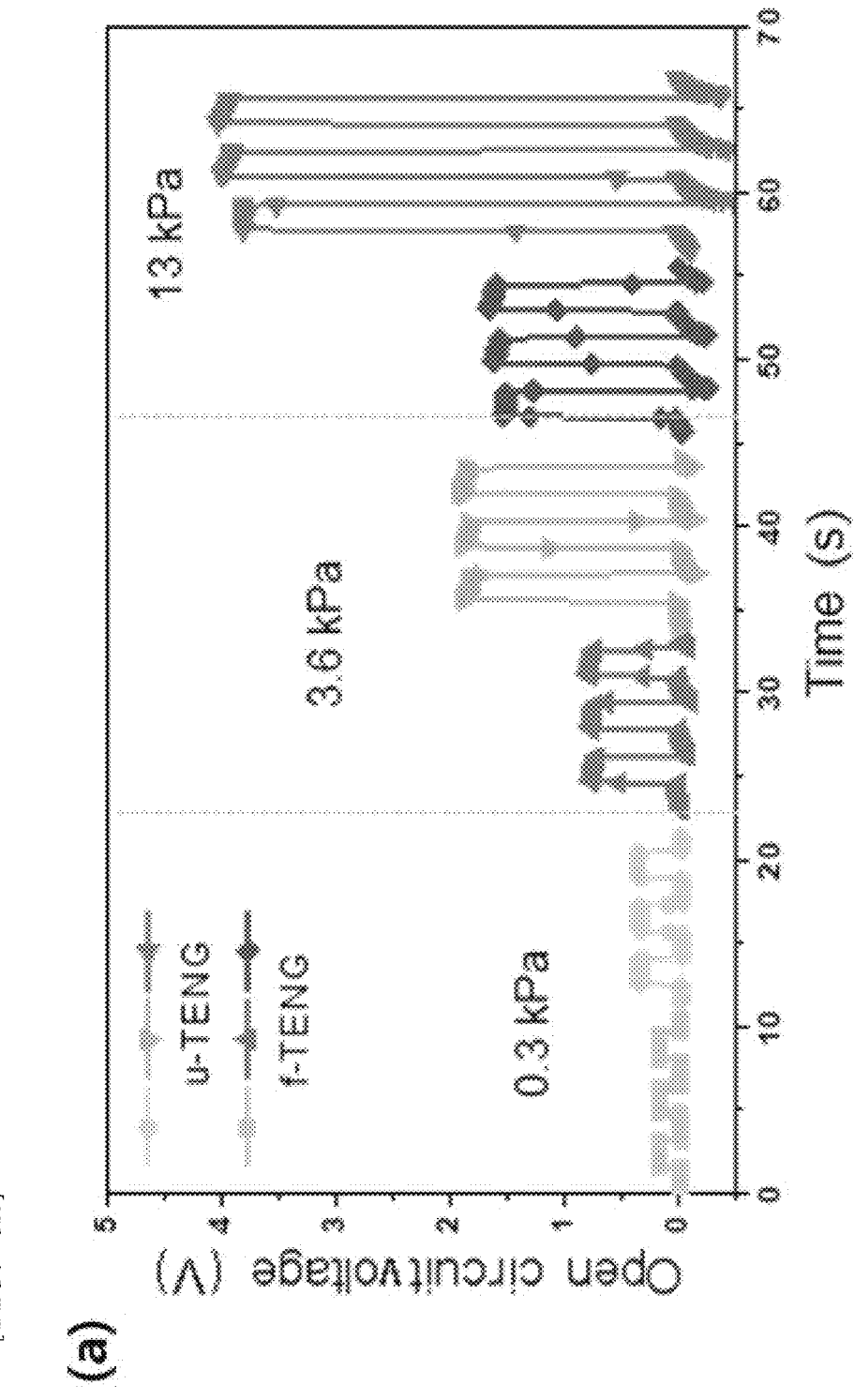

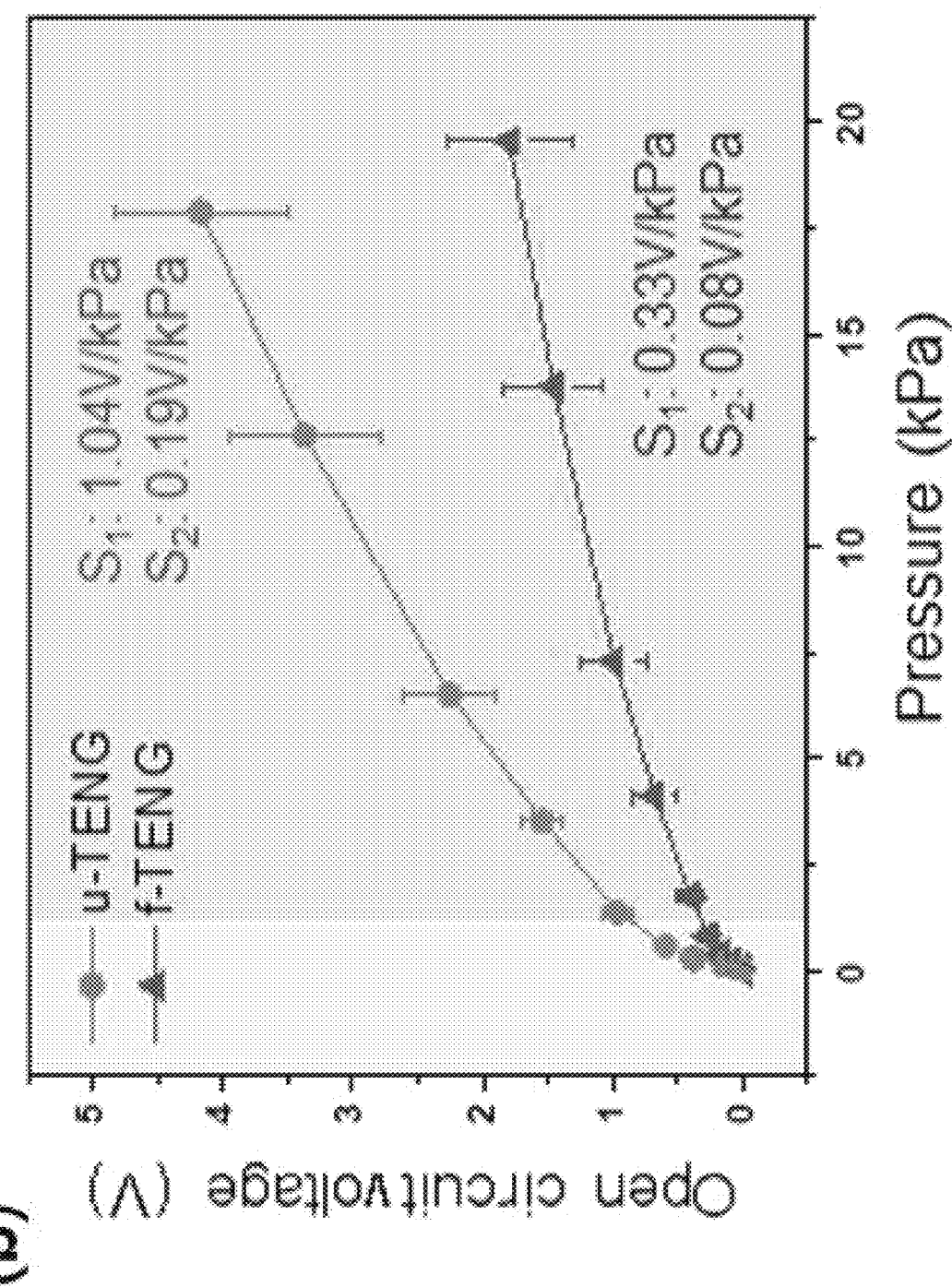
[FIG. 5B]
(b)

[FIG. 5C]
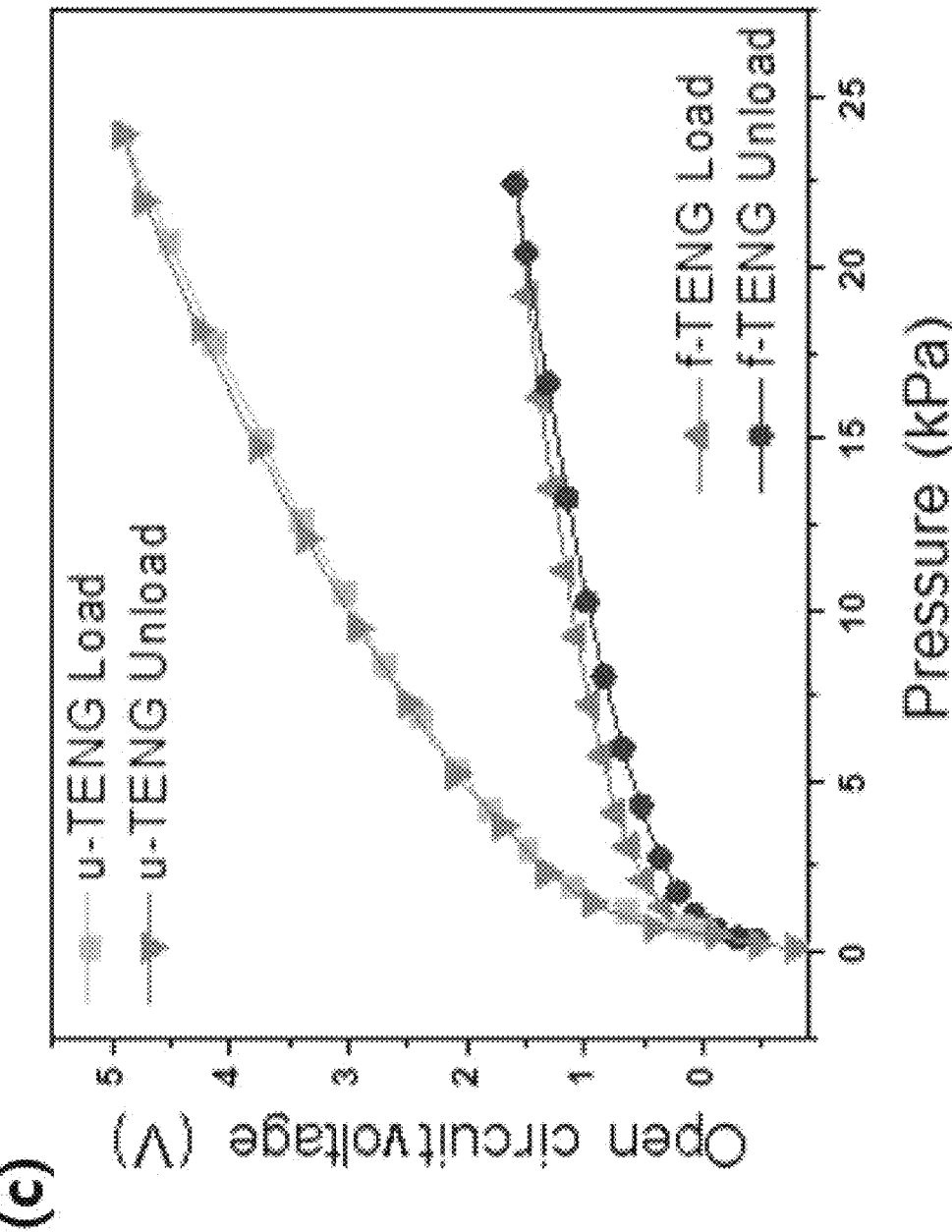
(c)

[FIG. 6]
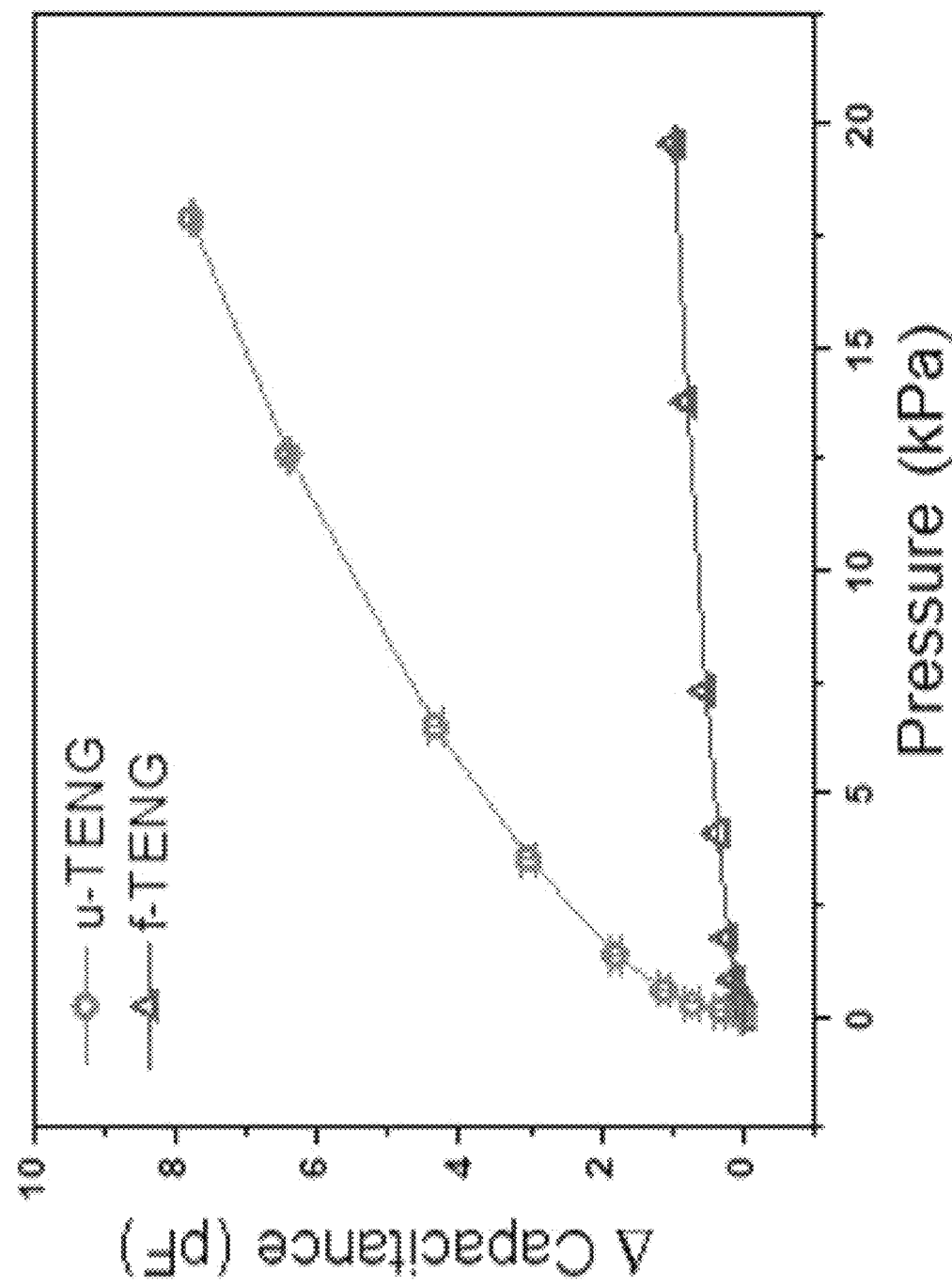

[FIG. 7]
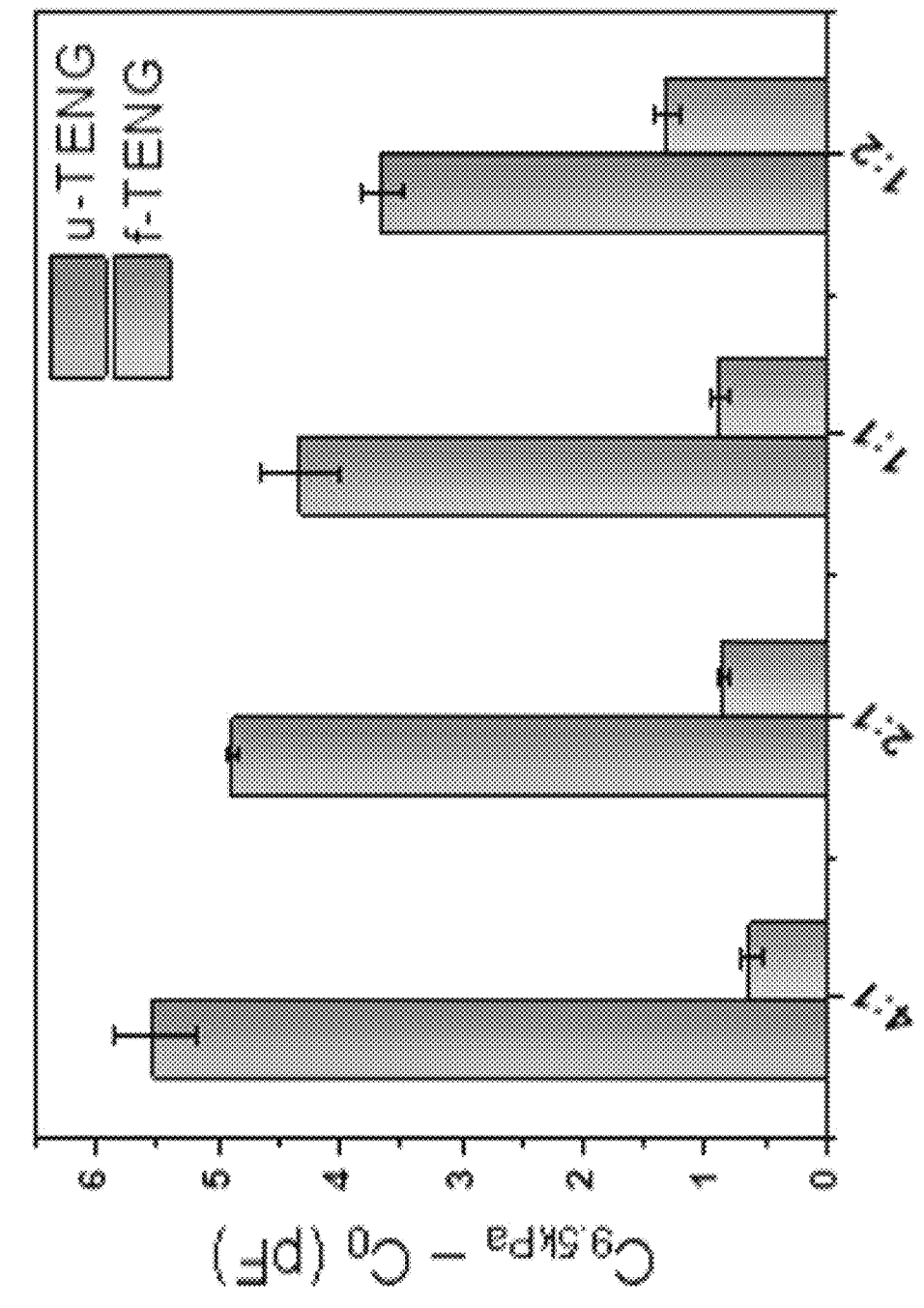

[FIG. 8A]
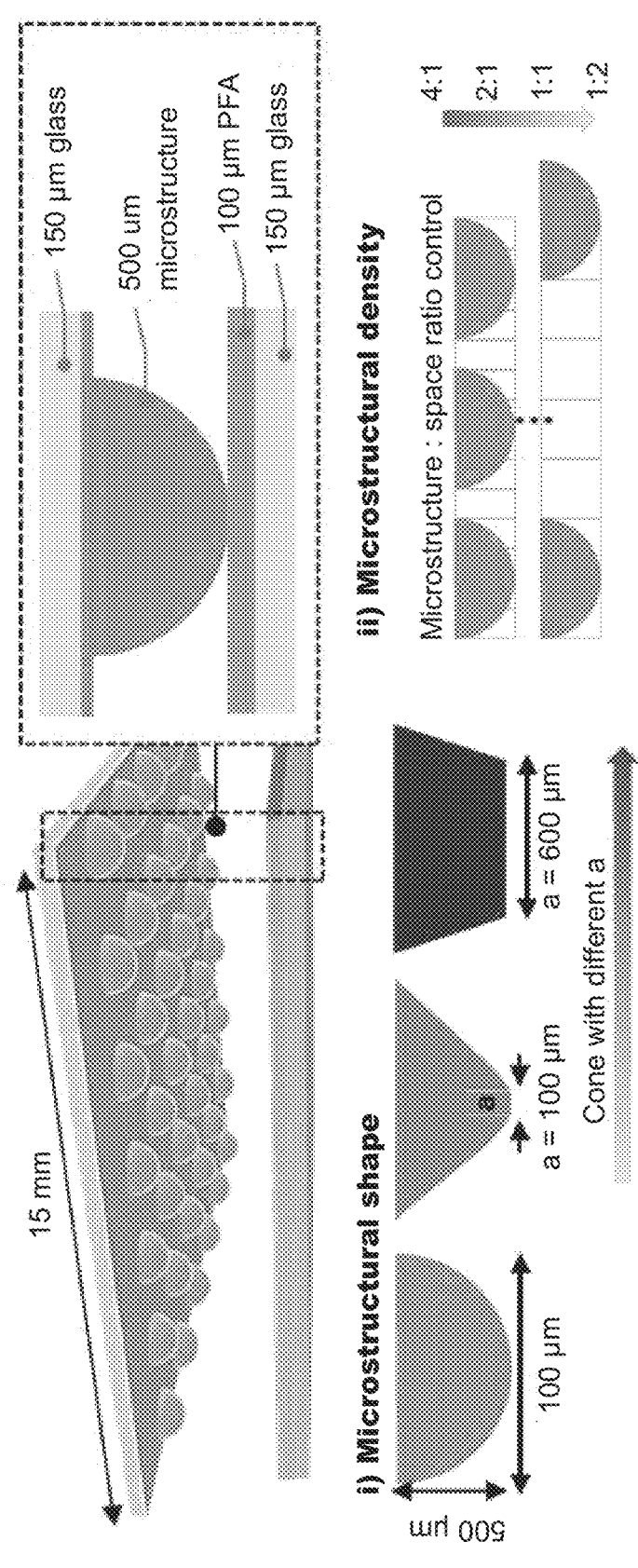

[FIG. 8B]
(b)
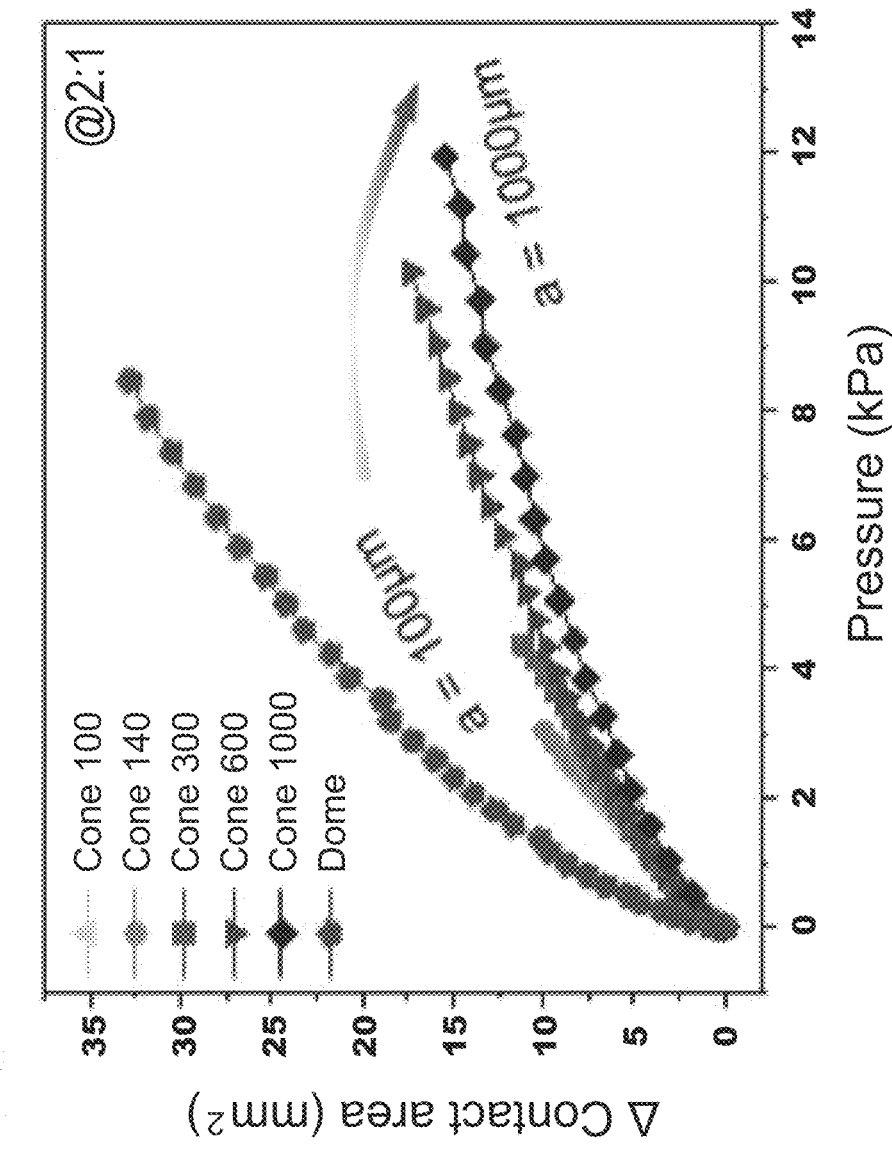

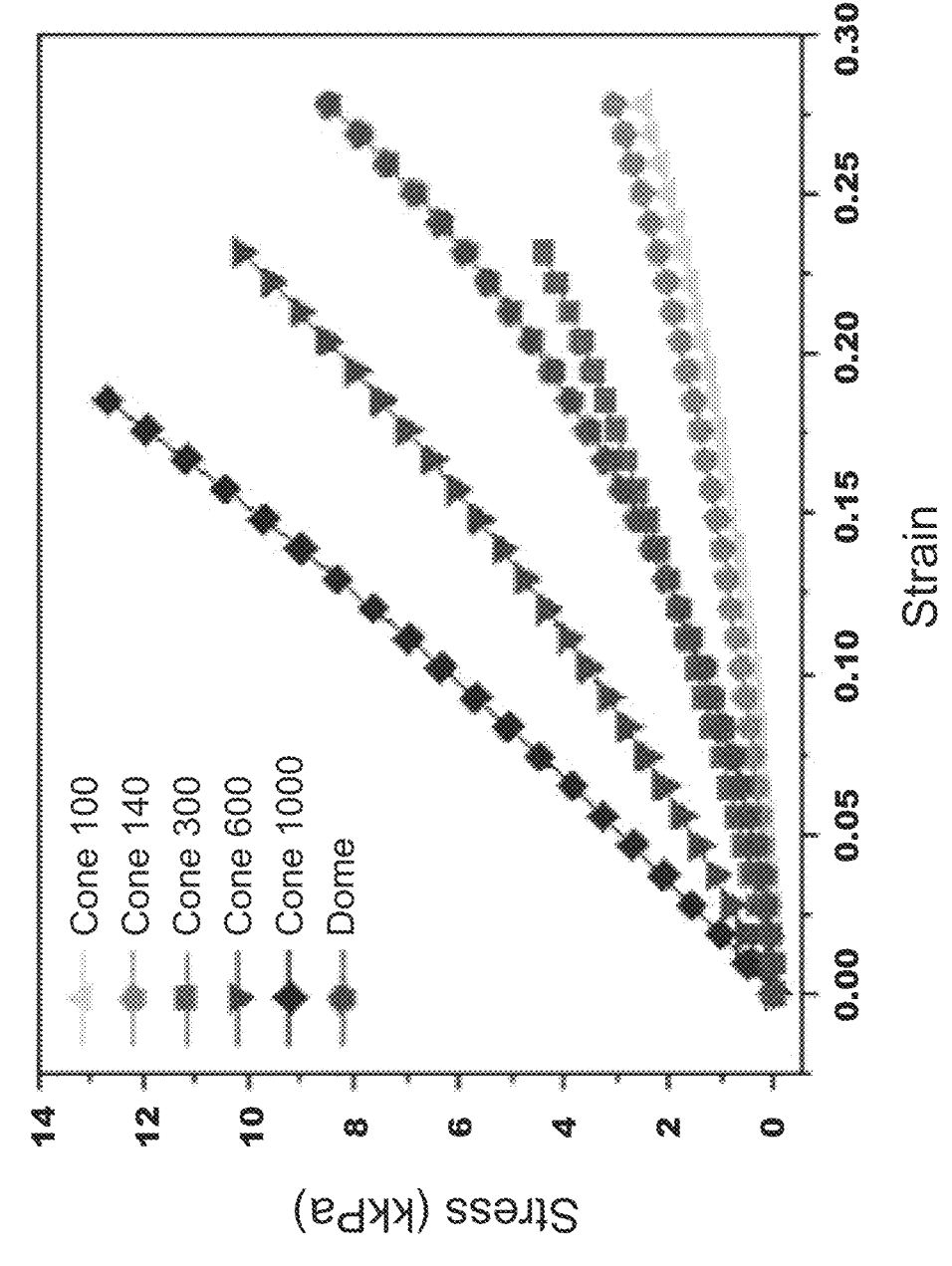

[FIG. 9A]
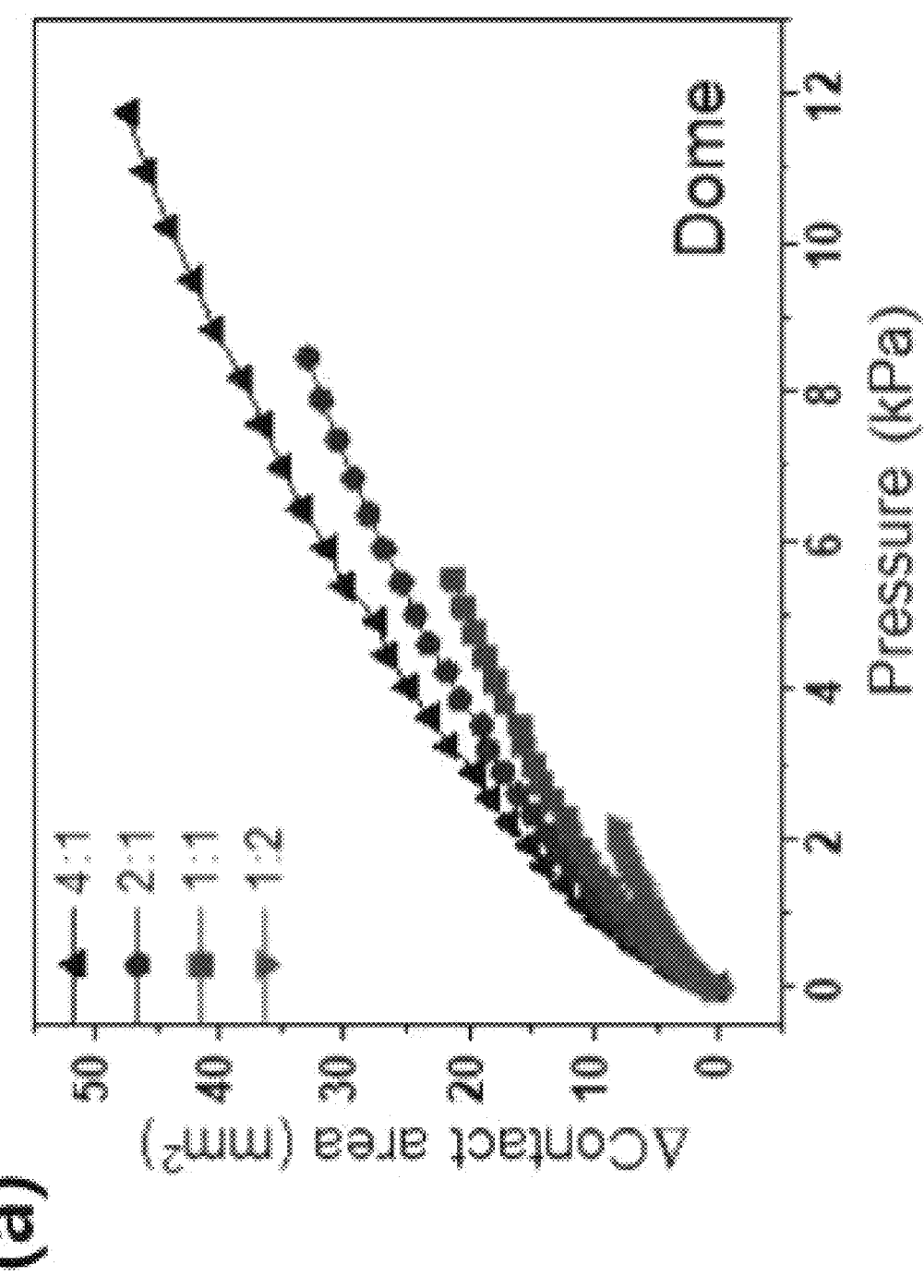
(a)

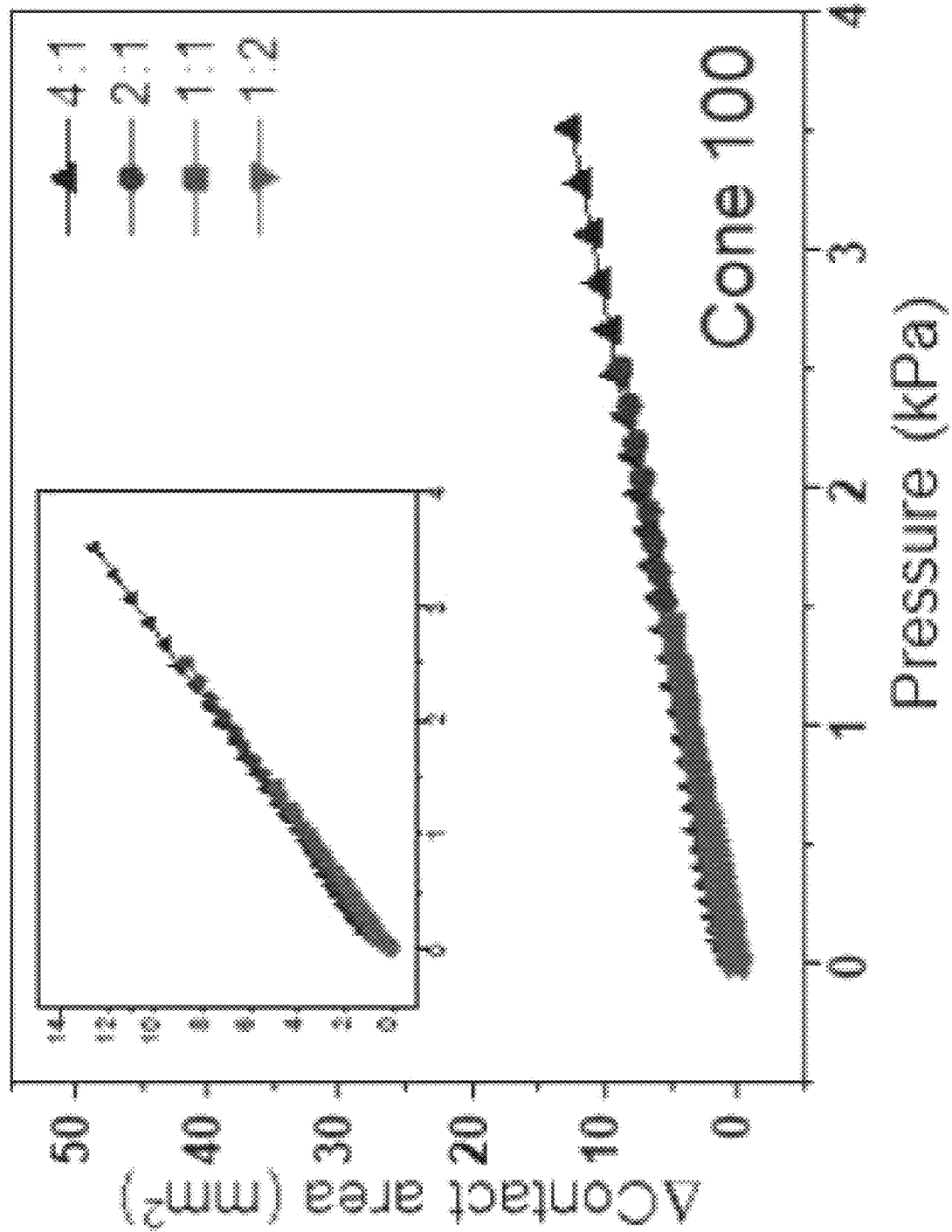
[FIG. 9A continued]

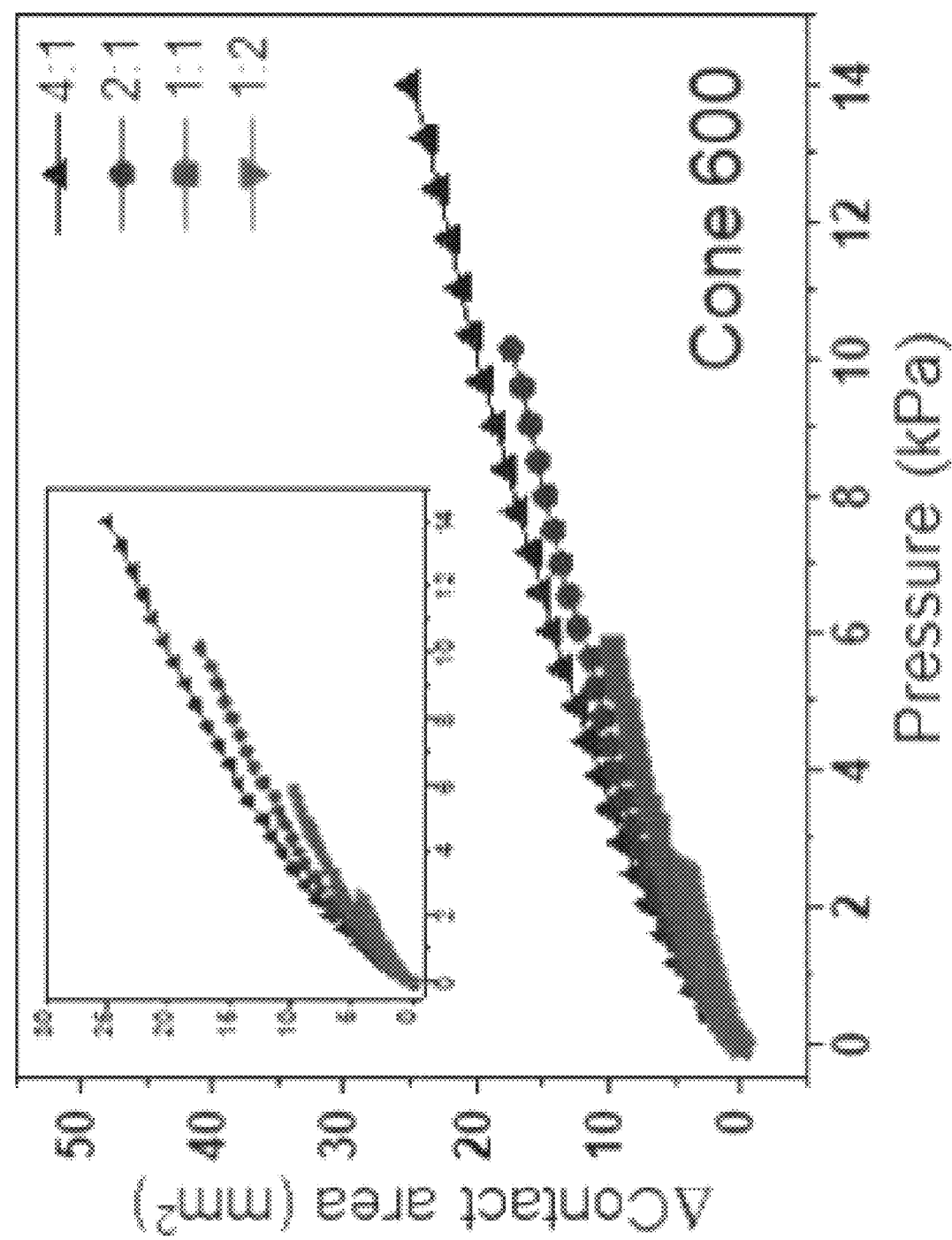
[FIG. 9A continued]

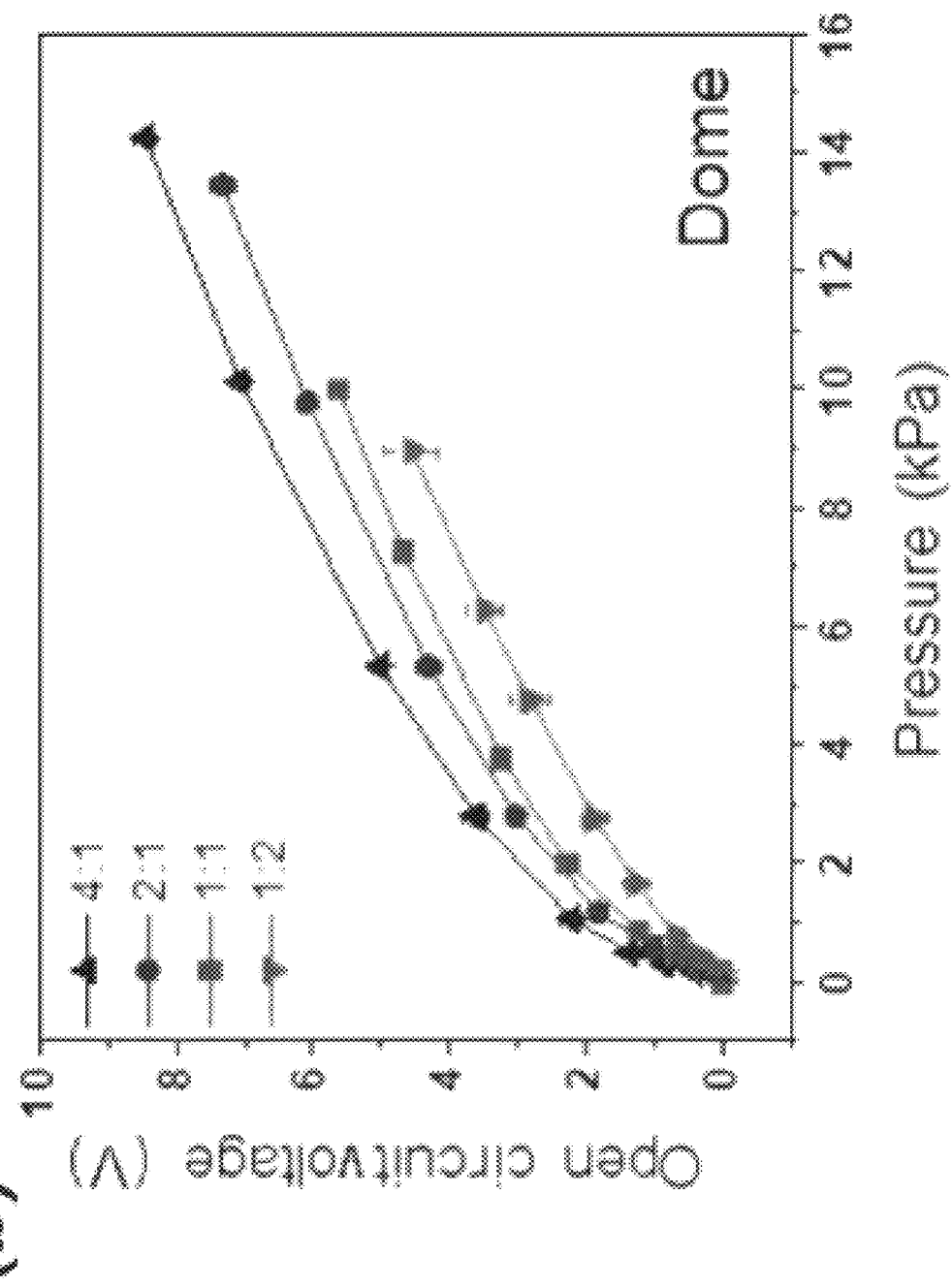
[FIG. 9B]

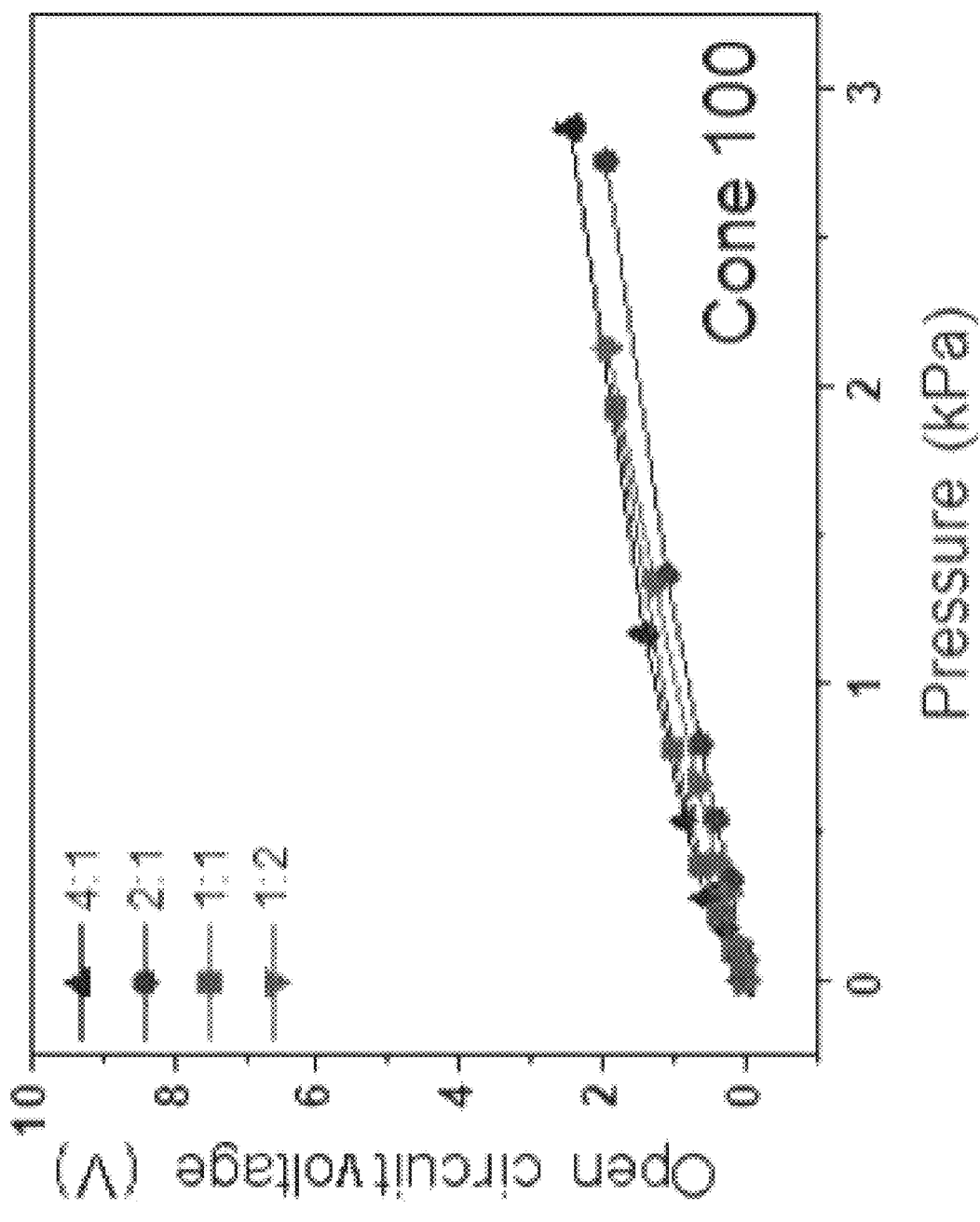
[FIG. 9B continued]

[FIG. 9B continued]
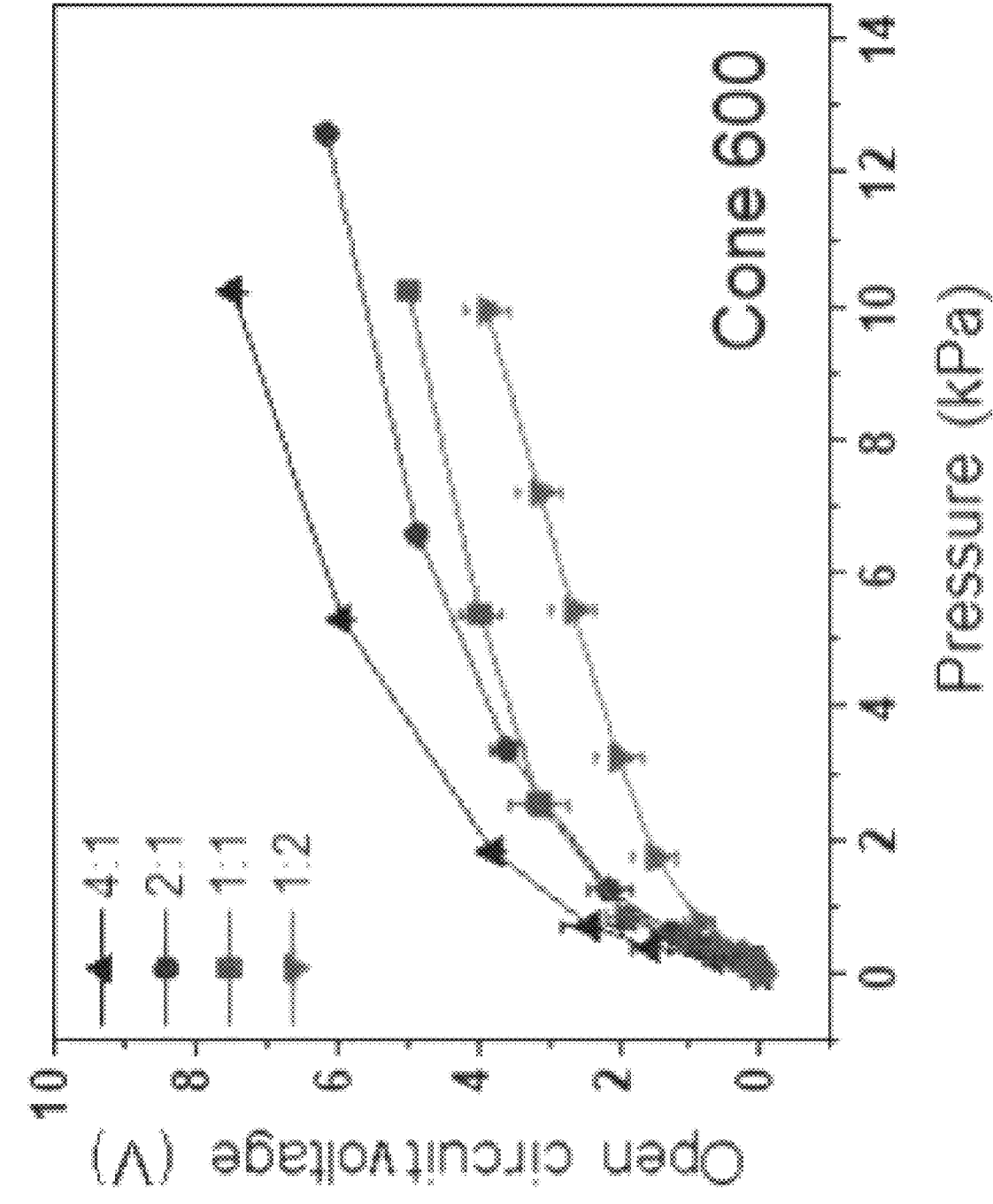

[FIG. 10A]
(a)
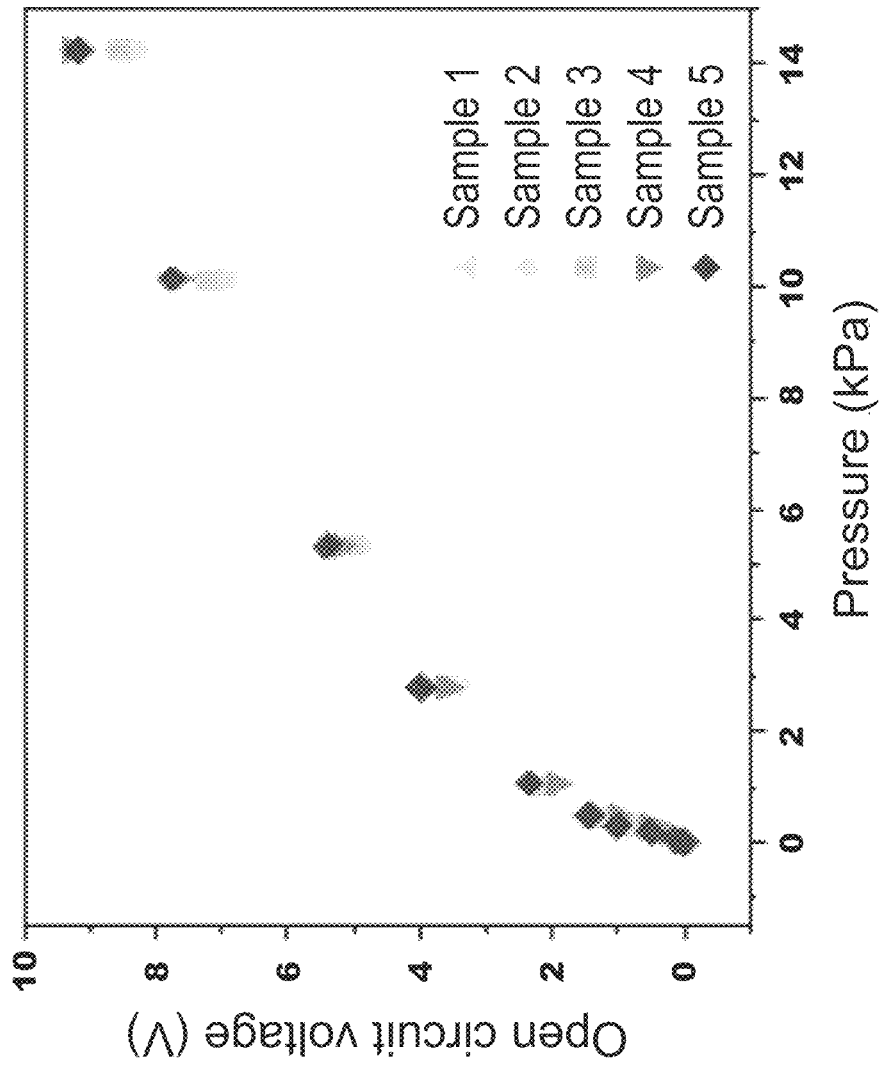

[FIG. 10B]
(b)
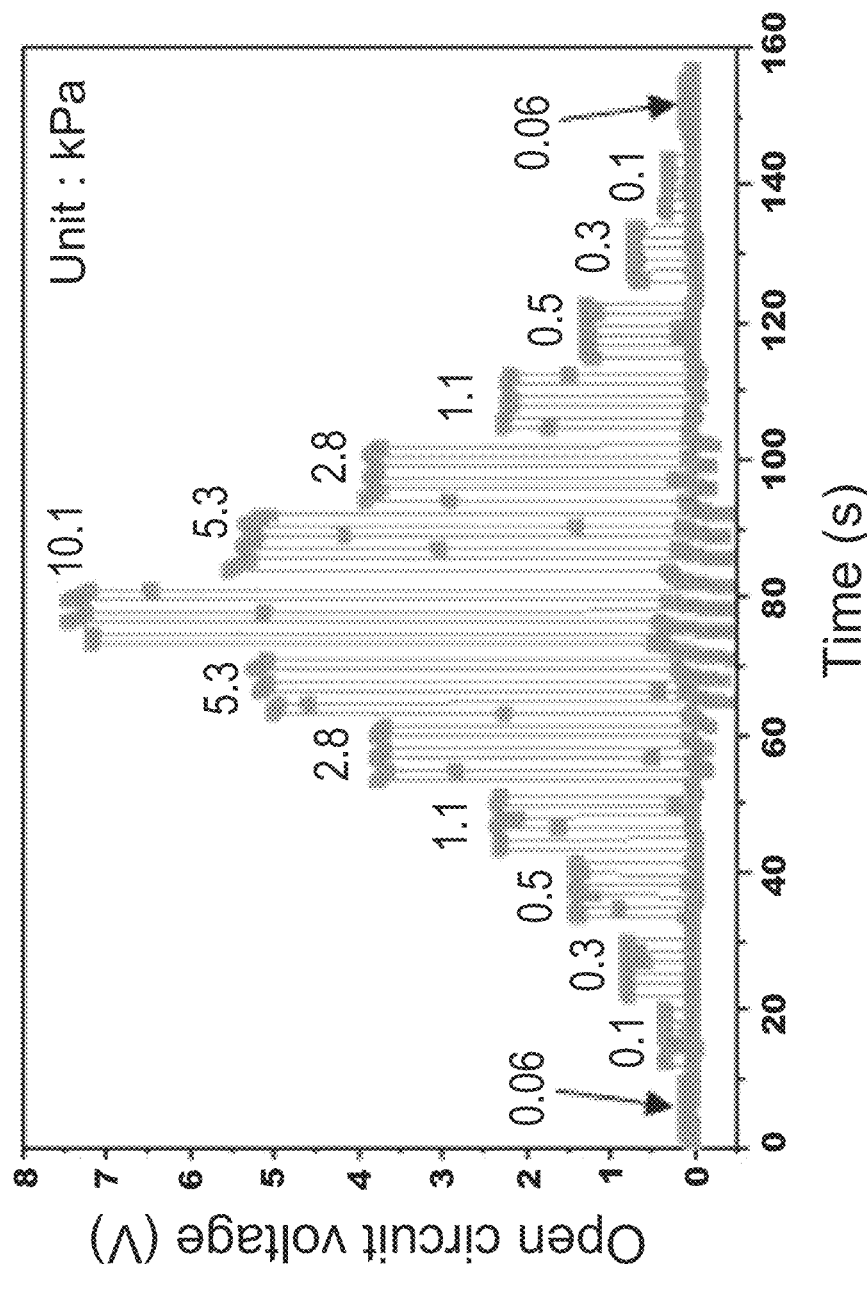

[FIG. 10C]
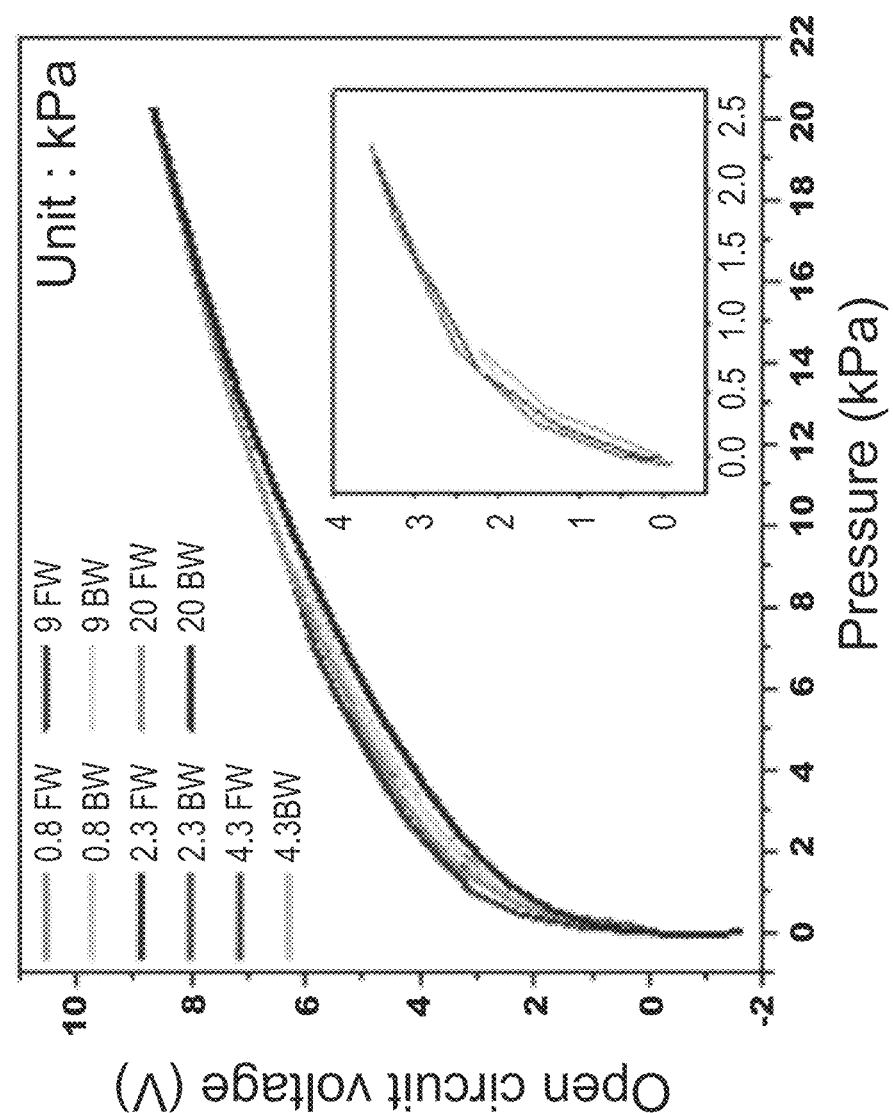

[FIG. 10D]
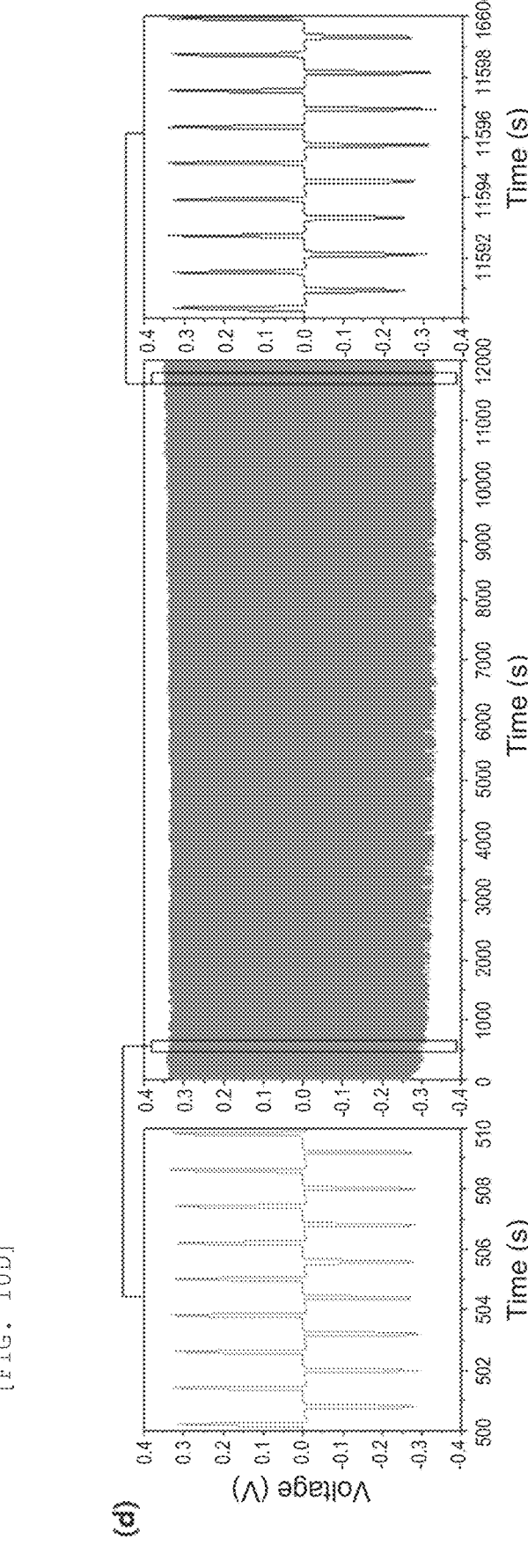

[FIG. 11]
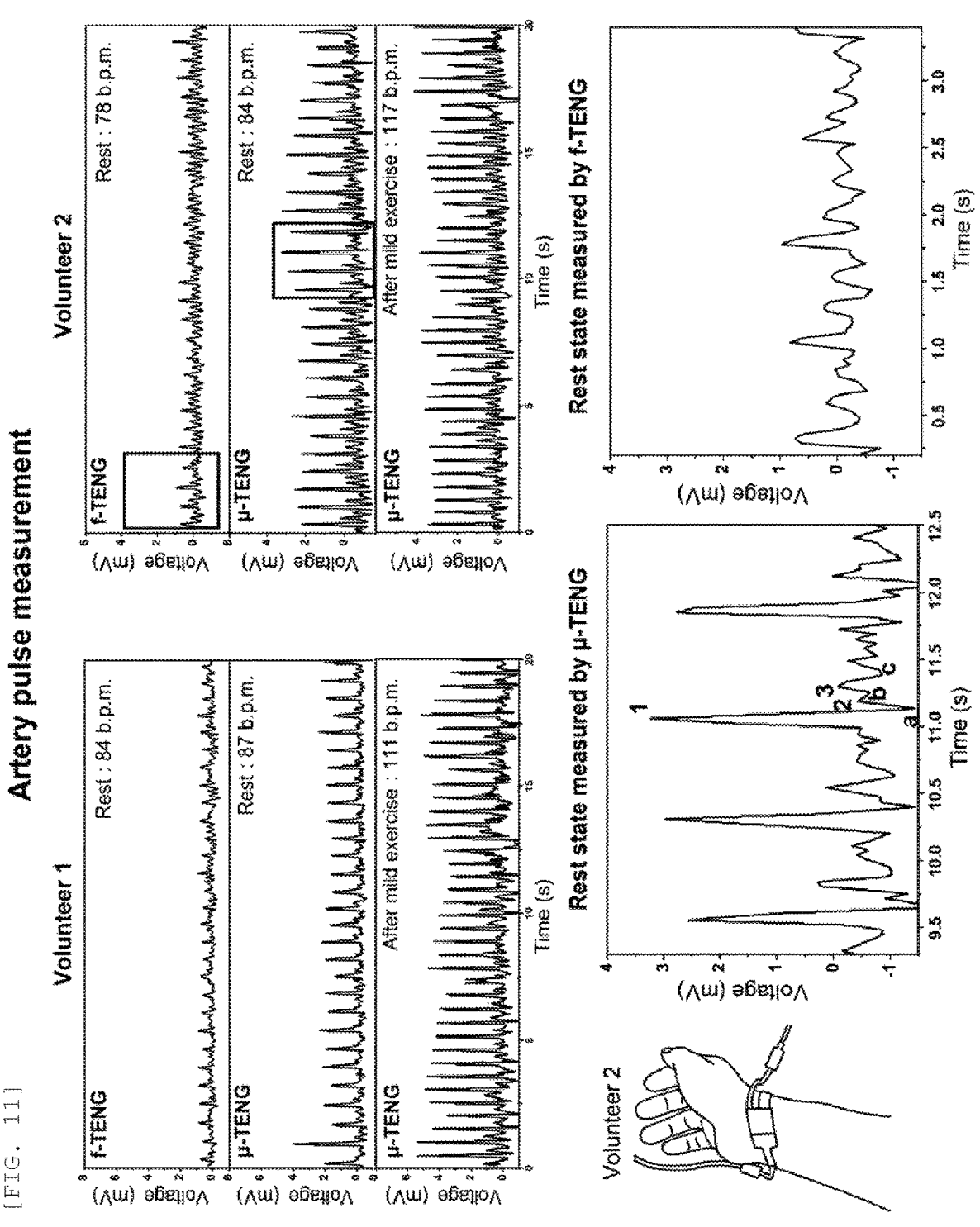

[FIG. 12]
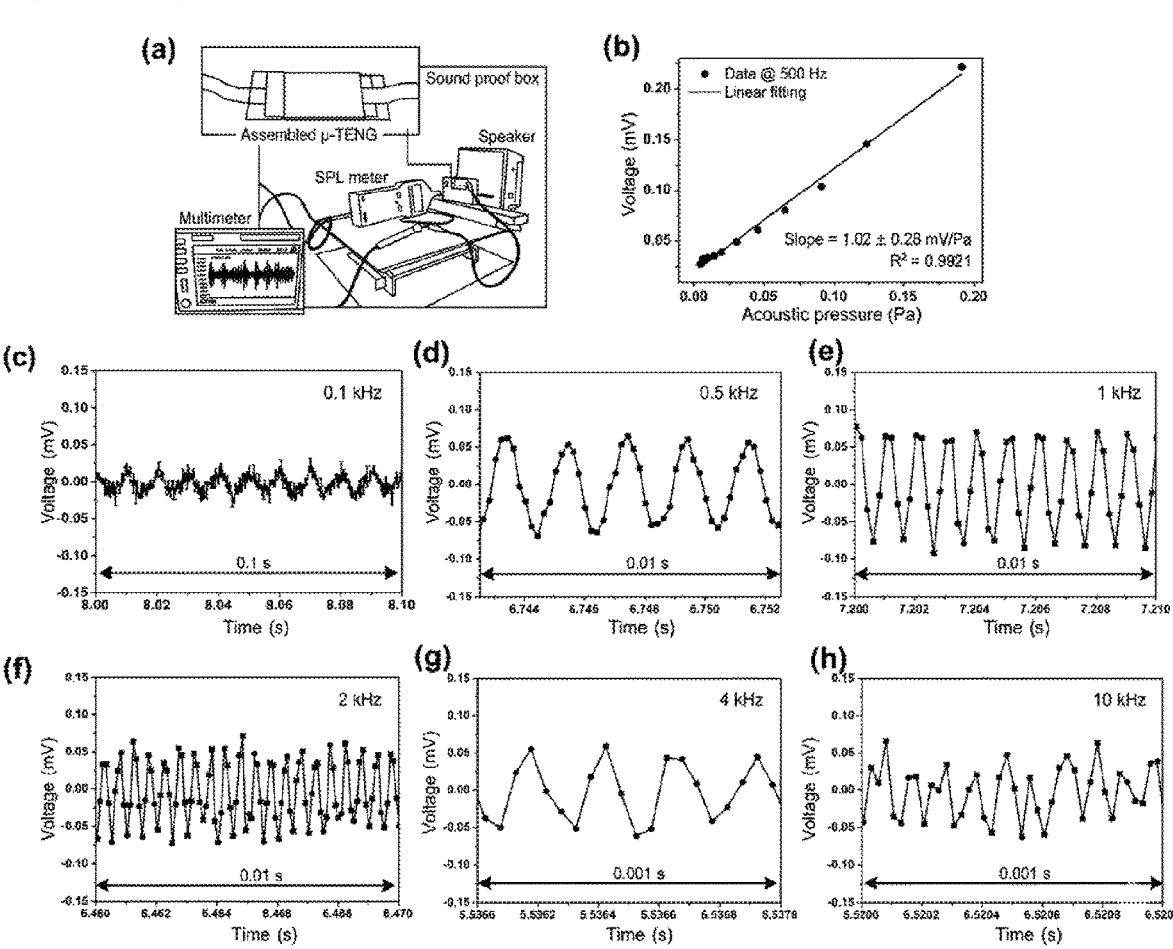

[FIG. 13]
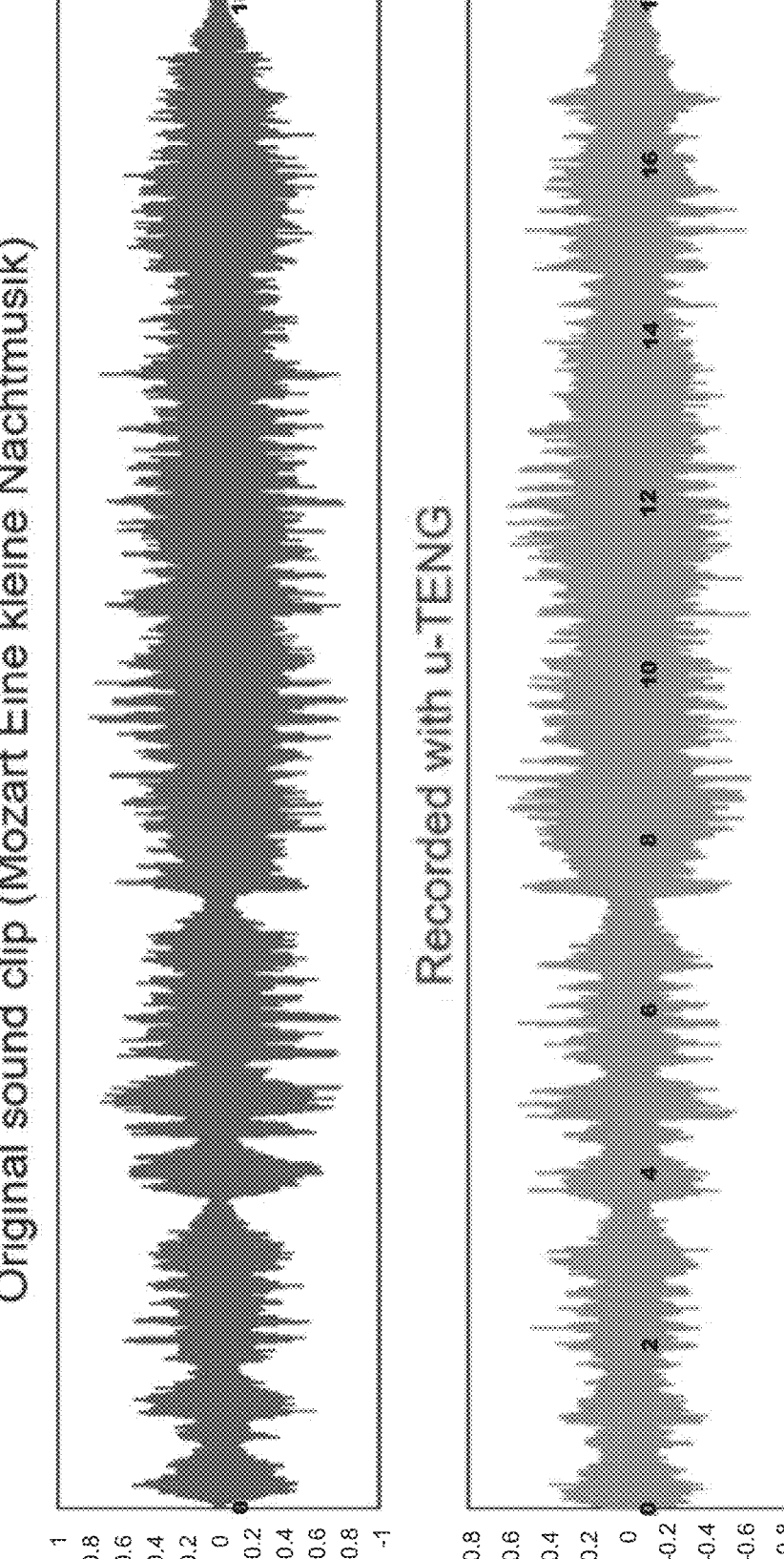

[FIG. 13 continued]
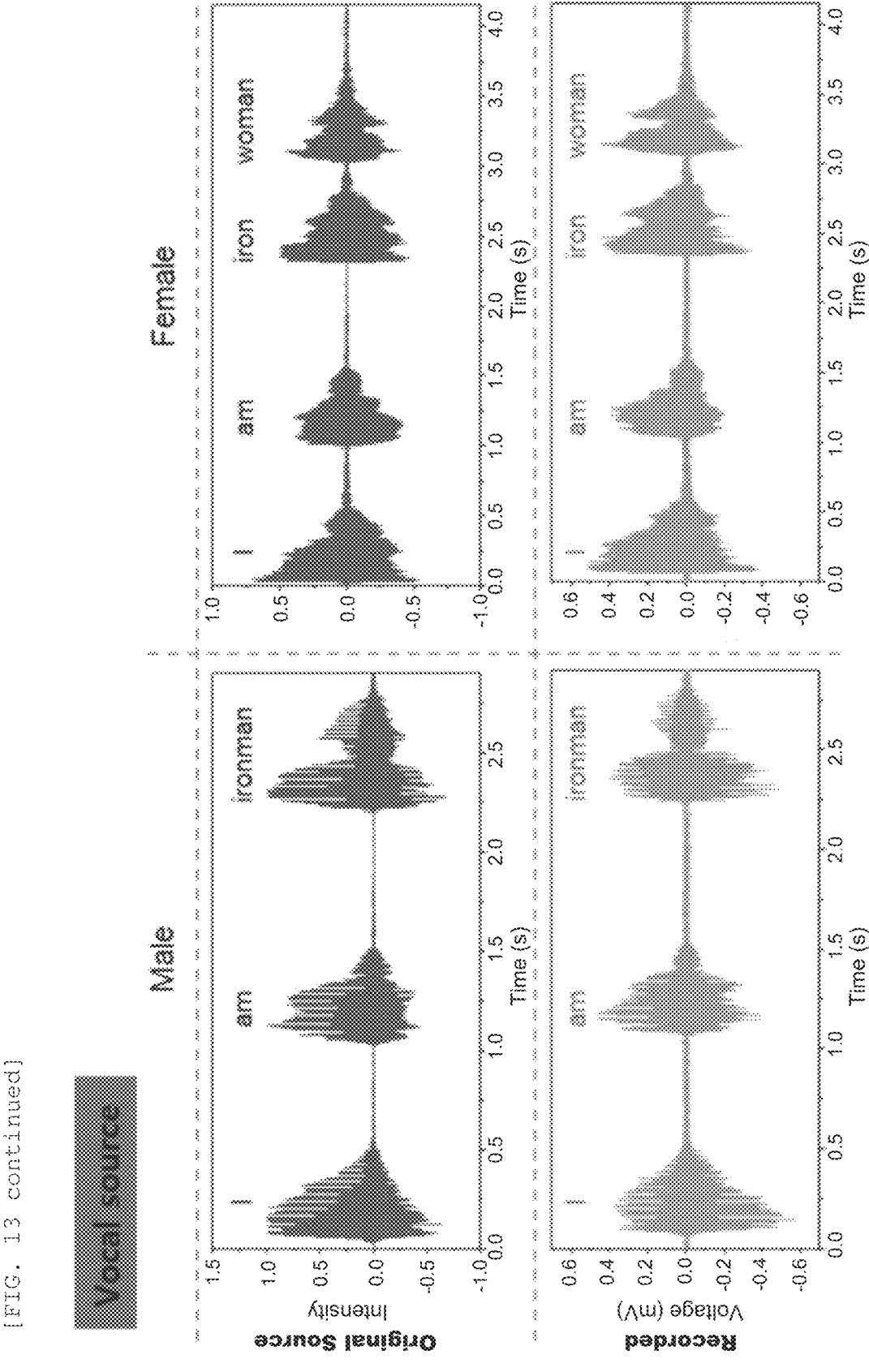

HIGHLY SENSITIVE SELF-POWERED PRESSURE SENSOR AND THE USE OF THE SAME

CROSS-REFERENCE TO RELATED APPLICATIONS

This application claims priority under 35 U.S.C. § 119 to Korean Patent Application No. 10-2022-0121816, filed on Sep. 26, 2022, in the Korean Intellectual Property Office, the disclosure of which is incorporated herein by reference in its entirety.

TECHNICAL FIELD

The following disclosure relates to a highly sensitive self-powered pressure sensor and the use of the same, and more particularly, to a highly sensitive self-powered pressure sensor using triboelectrification generation and the use of the same.

BACKGROUND

Pressure stimulation may have a wide spectrum, ranging from the smallest sound to a flow of fluid in the air, a pulse in a human body, a touch, or a footstep. There is a need for a small, wearable, and highly sensitive pressure sensor to predict an abnormal sign in the human body by detecting pressure stimulation having a range of a small vibration occurring inside and outside the body among the stimulations, or to acquire information from the outside.

Types of the pressure sensors may include a piezoresistive sensor and a capacitive sensor, which consume power, and a triboelectric sensor and a piezoelectric sensor, which are self-generating types that do not consume power. These sensors may each have different principles and features. Each of the piezoresistive, capacitive, and triboelectric pressure sensors may attempt to increase its sensitivity and sensing range by introducing a protrusion structure to output an electrical signal sensitively even at a low pressure, thereby respectively maximizing a change in contact resistance, a change in dielectric constant, and a change in an area of a friction surface.

However, these sensors may still have difficulty in achieving high sensitivity in a low pressure range because an active material showing the change in the area and an electrode detecting the change are far away from each other, thus making it impossible to fully utilize an advantage of the protrusion structure. In addition, the protrusion structure may be generally produced by etching a silicon (Si) wafer and using the same as a mold. Therefore, the protrusion structure implemented in a conventional study may be limited to a spherical, pyramidal, or cylindrical shape, which results in a limitation in implementing various appropriate structures required based on a type of the pressure stimulation.

SUMMARY

An embodiment of the present disclosure is directed to providing a highly sensitive self-powered pressure sensor capable of being operated by self-generation without a separate power supply.

Another embodiment of the present disclosure is directed to providing a self-powered pressure sensor having excellent reliability and durability.

In one general aspect, a self-powered pressure sensor includes: a first electrode; a first triboelectrification unit positioned on the first electrode; a second triboelectrification unit including a pattern on which a microstructure is repeatedly positioned, the microstructure being reversibly in contact with or separated from the first triboelectrification unit by a physical external force, and having at least one surface in contact with the first triboelectrification unit to induce a change in a contact area; and a second electrode positioned inside the second triboelectrification unit and conformally positioned on a surface of the microstructure, wherein the first electrode and the second electrode are geometrically asymmetric to each other.

The microstructure may have any one selected from sphere, hemisphere, cone, truncated cone, polygonal pyramid, and truncated polygonal pyramid shapes.

The microstructure may have the hemisphere or the truncated cone shape.

The microstructure may have the hemisphere shape.

A microstructure diameter may be 200 to 2000 μm and a microstructure height may be 100 to 3000 μm.

The first electrode may have a flat structure.

The first triboelectrification unit and the second triboelectrification unit may include different materials.

The first triboelectrification unit may include any one selected from the group consisting of fluorinated ethylene-propylene copolymer (FEP), polyvinylidene fluoride (PVDF), perfluoroalkoxy alkane (PFA), and ethylene-tetrafluoroethylene copolymer (ETEF).

The second triboelectrification unit may include a siloxane-based polymer.

The second electrode may include a metal nanowire.

A separation distance between the surface of the microstructure and the second electrode may be 1 to 30 μm.

A thickness of the second electrode may be 0.5 to 2 μm.

A ratio of the thickness of the second electrode to the separation distance between the surface of the microstructure and the second electrode may be 1:1 to 30.

Elastic modulus of the first triboelectrification unit may be $10^2$ times or more than that of the second triboelectrification unit.

The microstructure may be repeatedly positioned on the pattern for a ratio of a microstructure diameter to a separation distance between the closest microstructures to be 1:0.25 to 2.

The self-powered pressure sensor may have pressure sensitivity of 0.1 to 5 V/kPa when a pressure is applied thereto.

In another general aspect, a sensor for pulse or acoustic pressure detection includes the self-powered pressure sensor described above.

BRIEF DESCRIPTION OF THE DRAWINGS

FIG. 1 is a schematic view schematically showing a series of processes where a u-electrode structure is produced including an electrode embedded in polydimethylsiloxane (PDMS) produced according to an embodiment of the present disclosure.

FIG. 2 shows the schematic view and scanning electron microscope (SEM) image of a self-powered pressure sensor of Inventive Example 1.

FIG. 3 is a view showing an operation mechanism of a u-triboelectric nanogenerator (u-TENG) system having a dual-electrode structure that includes a u-electrode structure as a second electrode.

FIG. 4 is a view schematically showing a change when a pressure is applied to the u-TENG system and an f-TENG system having a dual-electrode structure that includes a flat structure electrode (f-electrode) as the second electrode.

FIGS. 5A, 5B, and 5C are views each showing an open circuit voltage (real-time Voc) reacting in real time, an open circuit voltage, and a hysteresis curve of the open circuit voltage, based on an applied voltage.

FIG. 6 is a view showing a capacitance change amount based on an applied pressure.

FIG. 7 is a view showing a capacitance change amount measured when applying a pressure of 9.5 kPa compared to capacitance before applying a pressure for Examples 1 to 4 and Comparative Examples 1 to 4.

FIG. 8A is a view schematically showing a shape of the microstructure, and FIGS. 8B and 8C are views respectively showing a change in a contact area and a strain-stress curve based on a pressure acquired through simulation of a structure including a positive pattern having a shape of each microstructure.

FIGS. 9A and 9B are views respectively comparing the change in the contact area based on the pressure acquired through the simulation and the open circuit voltage based on the pressure acquired through the measurement.

FIG. 10A, FIG. 10B, FIG. 10C, and FIG. 10D are views respectively showing a reproducibility result of five different samples each prepared according to Example 1, a measurement result of an open circuit voltage measured in real time based on pressure levels from 0.06 to 10.1 kPa, hysteresis curves respectively acquired by setting pressures of 0.8 to 20 kPa as the maximum loading pressure, and a result of long-term stability tests for 10,000 cycles by using one cycle of loading/unloading a pressure of 10 kPa.

FIG. 11 is a view showing sensing sensitivity when self-powered pressure sensors produced according to Example 1 and Comparative Example 1 are applied for pulse detection.

FIG. 12A is a view showing an experimental setup for evaluating detection performance of an acoustic pressure, FIG. 12B is a view showing a voltage output based on a pressure of an acoustic pressure at a frequency of 500 Hz, and FIGS. 12C to FIG. 12H are views respectively showing temporal response results of the pressure sensor at frequencies of 0.1 kHz, 0.5 kHz, 1 kHz, 2 kHz, 4 kHz, and 10 kHz.

FIG. 13 is a view comparing waveforms of actual sound sources for music and voice with waveforms of sound sources for music and voice recorded using the self-powered pressure sensor.

DETAILED DESCRIPTION OF EMBODIMENTS

Hereinafter, a self-powered pressure sensor of the present disclosure will be described in detail with reference to the attached drawings.

The accompanying drawings below are provided by way of example so that the spirit of the present disclosure may be sufficiently transferred to those skilled in the art to which the present disclosure pertains. Therefore, the present disclosure is not limited to the accompanying drawings provided below, and may be modified in many different forms. In addition, the accompanying drawings suggested below will be exaggerated in order to clear the spirit of the present disclosure.

Technical terms and scientific terms used herein have the general meanings understood by those skilled in the art to which the present disclosure pertains unless otherwise defined, and a description of the known function and configuration which may unnecessarily obscure the gist of the present disclosure will be omitted in the following description and the accompanying drawings.

In addition, a term of a singular number as used in the specification and the appended claims is intended to include its plural number unless the context clearly indicates otherwise.

Terms "first," "second," and the like may be used in the specification and the appended claims to distinguish one component from another component rather than limiting the corresponding component.

It is to be understood that a term "include," "have," or the like used in the specification and the appended claims specifies the existence of features or components, mentioned in the specification, and does not preclude possible addition of one or more other features or components, unless specifically limited.

In the specification and the appended claims, when a part such as a film (layer), a region, a component, or the like is referred to as being 'on' another part, it indicates not only a case where the corresponding component is directly on the another part, but also a case where another film (layer), another region, or another component is interposed therebetween.

A self-powered pressure sensor according to an embodiment of the present disclosure may include: a first electrode; a first triboelectrification unit positioned on the first electrode; a second triboelectrification unit including a pattern on which a microstructure is repeatedly positioned, the microstructure being reversibly in contact with or separated from the first triboelectrification unit by a physical external force, and having at least one surface in contact with the first triboelectrification unit to induce a change in a contact area; and a second electrode positioned inside the second triboelectrification unit and conformally positioned on a surface of the microstructure, wherein the first electrode and the second electrode are geometrically asymmetric to each other.

A high-performance pressure sensor is developed based on various sensing mechanisms such as capacitance, resistance, piezoelectricity, or triboelectricity to precisely detect a physical signal such as a blood pressure or a heart rate.

However, a sensor detecting the pressure based on a change in the capacitance or a change in the resistance may require power consumption to its operation, which limits its use.

Accordingly, a pressure sensor using the triboelectricity and capable of being self-generated is spotlighted as the high-performance pressure sensor.

In general, a principle of the sensor operated based on triboelectric nanogenerators (TENG) may be divided based on its structure. The sensor may be operated in the following modes: a vertical contact-separation mode in which a potential difference generated by triboelectric charges generated on the two surfaces of the sensor in a process in which these two contact surfaces are repeatedly in contact with each other and separated from each other in a vertical direction; a lateral sliding mode in which the potential difference is generated due to an imbalance in the triboelectric charges produced as the two surfaces in contact with each other are laterally moved; or a single electrode mode in which a single electrode is provided.

Spotlighted is the self-powered pressure sensor based on the vertical contact-separation mode among these modes, in which the sensor may detect various types of pressures and output a relatively highest electrical signal.

However, most of the self-powered pressure sensors based on the vertical contact-separation mode may be designed so that a surface of the charged material has various structural shapes to improve the contact area by deformation of the charged material. However, the paired electrodes positioned to be opposite to each other may be flat, and have a geometrically symmetric structure on an opposite surface of the charged material on which the structure is positioned.

On the other hand, the self-powered pressure sensor according to an embodiment of the present disclosure, may have the geometrically asymmetric structure of the first electrode and the second electrode opposing each other, the second electrode being conformally positioned on the surface of the microstructure included in the second triboelectrification unit. Accordingly, the sensor may provide excellent pressure sensitivity by significantly improving a change rate of the capacitance compared to the prior art due to increase in a parallel electric field region induced by the change in the contact area of the second triboelectrification unit when the pressure is applied thereto, and significantly improving transfer efficiency of the charges generated by the potential difference generated by triboelectrification.

In addition, the second electrode may be positioned inside the second triboelectrification unit to improve durability and reliability of the self-powered pressure sensor during its long-term operation.

In an embodiment, the first triboelectrification unit and the second triboelectrification unit may include different materials.

Each triboelectrification unit may be charged with complementary charges when the first triboelectrification unit and the second triboelectrification unit come into contact with each other. Here, a polarity of each triboelectrification unit may be determined by charging heat based on a feature of sending out or attracting electrons. That is, the first triboelectrification unit and the second triboelectrification unit may each include materials having a large difference in polarity based on the charging heat.

As a specific example, the first triboelectrification unit may include any one selected from the group consisting of fluorinated ethylene-propylene copolymer (FEP), polyvinylidene fluoride (PVDF), perfluoroalkoxy alkane (PFA), and ethylene-tetrafluoroethylene copolymer (ETEF).

In an advantageous example, the first triboelectrification unit may include perfluoroalkoxy alkane.

The first triboelectrification unit may need to have an excellent mechanical feature such as elastic modulus in order to stably induce deformation of the second triboelectrification unit by its contact with the second triboelectrification unit described below in addition to generation efficiency of the triboelectric charges through the contact. It may be advantageous in improving the sensitivity of the self-powered pressure sensor by satisfying the above-mentioned feature when perfluoroalkoxy alkane is included in the first triboelectrification unit.

Here, the elastic modulus of the first triboelectrification unit may be $10^2$ times or more, $10^3$ times or more, or $10^4$ times or more than that of the second triboelectrification unit, and its upper limit is not limited, and may be $10^{10}$ times or less.

As the elastic modulus of the first triboelectrification unit and that of the second triboelectrification unit satisfy the above-mentioned range, the deformation of the second triboelectrification unit may be stably induced, thus making it possible to detect a minute change in the pressure.

For example, the elastic modulus of the first triboelectrification unit may be 300 MPa or more, 500 MPa in detail, may have no upper limit, and may be 10 GPa or less.

In addition, the first triboelectrification unit may have a flat structure with a thickness of 50 to 500 μm, substantially 80 to 150 μm.

As a specific example, the first triboelectrification unit may be positioned on the first electrode.

Here, the first electrode may have the flat structure, similar to the first triboelectrification unit.

For example, the thickness of the first electrode may be 50 to 500 μm, 100 to 300 μm in detail, and the present disclosure is not limited by the thickness of the first electrode.

As a specific example, the first electrode may include any conductive material known in the art without limitation, and as a non-limiting example, the first electrode may be any one or two or more selected from fluorine-containing tin oxide (FTO), indium-containing tin oxide (ITO), indium-containing zinc oxide (IZO), aluminum-containing zinc oxide (AZO), and a composite thereof.

In an embodiment, the second triboelectrification unit may include an elastomer-based polymer that may be easily deformed by its contact with the first triboelectrification unit.

For example, the elastomeric polymer may be one or more selected from polyacrylate rubber (ACM), ethylene acrylic rubber (AEM), polyester urethane (AU), butadiene rubber (BR), chloroprene (or neoprene) rubber, CR), chlorosulfonated polyethylene (CSM), ethylene oxide epichlorohydrin rubber (ECO), ethylene propylene diene rubber (EPDM), polyether urethane (EU), perfluoroelastomer (FFKM), fluorocarbon rubber (FKM), fluorosilicone rubber (FVMQ), hydrogenated nitrile butadiene rubber (HNBR), isoprene rubber (IR), butyl rubber (IIR), nitrile butadiene rubber (NBR), natural rubber (NR), polydimethylsiloxane (PDMS), styrene butadiene rubber (SBR), polybutadiene (PB), polyurethane (PU), polyurethane acrylate (PUA), polyvinylidene fluoride (PVDF), polyvinylidenefluoride-co-trifluoroethylene (PVDF-TrFE), and silicone rubber (VMQ).

In an advantageous example, the second triboelectrification unit may include a siloxane-based polymer, and the siloxane-based polymer may be polydimethylsiloxane (PDMS).

In detail, the second triboelectrification unit may include the microstructure inducing the change in the contact area by its contact with the first triboelectrification unit. Here, the second electrode described below may be conformally positioned on the surface of the microstructure, and positioned on the second triboelectrification unit.

That is, the second triboelectrification unit may include a first region brought into direct contact with the first triboelectrification unit while having the second electrode therebetween, and a second region positioned to be opposite to the first region.

Here, the elastomeric polymers included in the first region and the second region may be the same or different from each other. However, it may be advantageous to include polydimethylsiloxane (PDMS) in at least the first region, brought into direct contact with the first triboelectrification unit, in consideration of the generation efficiency of the triboelectric charges and the deformation feature.

In an embodiment, the microstructure included in the second triboelectrification unit may have any one selected from sphere, hemisphere, cone, truncated cone, polygonal pyramid, and truncated polygonal pyramid shapes.

To improve a change degree in the contact area by the contact with the first triboelectrification unit, the microstructure included in the second triboelectrification unit may have the hemisphere or truncated cone shape.

Here, a truncated cone may indicate a shape in which one pointed end of a cone structure is cut, and its cut surface may be in contact with the first triboelectrification unit.

As a specific example, a diameter of the cut surface may be 10 to 1000 μm, 50 to 600 μm in detail, or 80 to 300 μm in more detail, and a diameter of an end surface positioned to be opposite to the cut surface may be 100 to 3000 μm, 200 to 2,000 μm in detail, 300 to 1000 μm in more detail, or 400 to 600 μm in even more detail.

In addition, a height of the truncated cone may be 100 to 3,000 μm, 200 to 2000 μm in detail, 300 to 1000 μm in more detail, or 400 to 600 μm in even more detail.

In an advantageous example, the microstructure may have the hemisphere shape.

Here, the diameter and height of the hemisphere may be the same as each other, and may be 100 to 3000 μm, 200 to 2000 μm in detail, 300 to 1000 μm in more detail, or 400 to 600 μm in even more detail.

The second triboelectrification unit may detect wide range of applied pressure with high sensitivity by including the hemispherical microstructure having the above-mentioned size (i.e., diameter and height).

In an embodiment, the second triboelectrification unit may include the pattern on which the above-mentioned microstructure is repeatedly positioned.

Here, density of the pattern, that is, the number of microstructures included for each unit area may be defined as a ratio of a microstructure diameter to a separation distance between the closest microstructures.

As a specific example, the ratio of the microstructure diameter to the separation distance between the closest microstructures may be 1:0.1 to 4, 1:0.1 to 2 advantageously, 1:0.1 to 0.5 more advantageously, or 1:0.1 to 0.3 even more advantageously.

The second triboelectrification unit may include the pattern on which the microstructure is repeatedly positioned so that the ratio of the microstructure diameter to the separation distance between the closest microstructures satisfies the above-mentioned conditions, thus improving its sensitivity to the wide range of applied pressure.

In a specific example, the number of microstructures included in the second triboelectrification unit of an area of 15 mm×15 mm may be 20 to 200, preferably 60 to 160, and more preferably 130 to 150.

In an embodiment, the second electrode conformally positioned on the surface of the microstructure may be positioned inside the second triboelectrification unit.

Here, the fact that the second electrode is conformally positioned on the surface of the microstructure may indicate that a second electrode layer having a structure parallel to that of the surface of the microstructure is positioned.

That is, the second electrode may be an electrode layer positioned inside the second triboelectrification unit that includes the microstructure, and having the same structure as that of the surface of the microstructure.

In an embodiment, the second electrode may include a metal nanowire.

As described above, in response to the applied pressure, the first triboelectrification unit and the second triboelectrification unit may be in contact with each other, thus inducing deformation of the microstructure included in the second triboelectrification unit. Here, the second electrode conformally positioned on the surface of the microstructure may be deformed to be the same as the microstructure as the second electrode is positioned inside the second triboelectrification unit.

Accordingly, the second electrode may require high flexibility as well as excellent conductivity, and thus advantageously include the metal nanowire in the second electrode to satisfy this requirement.

For example, the metal nanowire may include one or more metals selected from silver, gold, platinum, and copper. In addition, the metal nanowire may include two types of metals among the above-mentioned metals, and the two types of metals may form a core-shell structure.

As a non-limiting example, a diameter of the metal nanowire may be 10 to 1,000 nm, and 100 to 500 nm in detail, and its aspect ratio may be 5 to 100, and 10 to 50 in detail. However, the present disclosure is not limited by the diameter and/or aspect ratio of the metal nanowire.

As a specific example, a thickness of the second electrode including the metal nanowire may be 0.01 to 10 μm, 0.1 to 5 μm in detail, or 0.5 to 2 μm in more detail.

As the thickness of the second electrode satisfies the above-mentioned range, the second electrode including the metal nanowire may have a network densely formed between the metal nanowires, and thus maintain an excellent electrical conductivity feature even though the second electrode is deformed along with the microstructure by the applied pressure.

In an embodiment, a separation distance between the surface of the microstructure and the second electrode may be 1 to 50 μm, 1 to 30 μm in detail, or 5 to 10 μm in more detail.

The separation distance between the surface of the microstructure and the second electrode may satisfy the above-mentioned range to significantly improve the transfer efficiency of the charges generated from the surface of the microstructure, thus further improving its sensitivity to the wide range of applied pressure.

In addition, it is possible to protect the second electrode positioned in the second triboelectrification unit from physical and/or chemical damage, which may not only improve the durability of the self-powered pressure sensor, but also provide reliable pressure detection even during its long-term use.

For example, a ratio of the thickness of the second electrode to the separation distance between the surface of the microstructure and the second electrode may be 1:0.5 to 50, 1:1 to 30 in detail, or 1:1 to 10 in more detail.

In an embodiment, the self-powered pressure sensor may have the pressure sensitivity of 0.1 to 5 V/kPa, and 0.1 to 3 V/kPa in detail, when the pressure is applied thereto. Here, the pressure sensitivity may indicate a voltage output for each unit pressure when the pressure is applied to the sensor.

In detail, the pressure sensitivity may appear differently based on a range of the applied pressure. When the applied pressure is 1 kPa or less, the pressure sensitivity may be 0.5 V/kPa or more, 0.6 V/kPa or more, 0.7 V/kPa or more, 0.8 V/kPa or more, 0.9 V/kPa or more, or 1.0 V/kPa or more, and may actually be 5 V/kPa or less.

When the applied pressure is more than 1 kPa, the pressure sensitivity may be 0.1 V/kPa or more, 0.12 V/kPa or more, 0.14 V/kPa or more, 0.16 V/kPa or more, 0.18 V/kPa or more, and may actually be 3 V/kPa or less.

The present disclosure may provide a sensor for pulse or acoustic pressure detection that includes the self-powered pressure sensor described above.

The sensor including the self-powered pressure sensor according to another embodiment of the present disclosure may detect a minute pressure, such as the pulse, with excellent sensitivity, and may also detect a sound wave, such as music or voice, with the excellent sensitivity.

In addition, the sensor including the self-powered pressure sensor according to another embodiment of the present disclosure may detect, with the excellent sensitivity, a wide spectrum of pressure, ranging from the above-mentioned minute pressure to a relatively high pressure such as vibration, touch, and footsteps occurring inside and outside a human body.

Hereinafter, the self-powered pressure sensor according to the present disclosure is described in more detail through Examples. However, Example described below is only a reference to explain the present disclosure in detail, the present disclosure is not limited thereto, and may be implemented in various forms.

In addition, unless otherwise defined, all technical and scientific terms may have the same meanings as those commonly understood by those skilled in the art to which the present disclosure pertains. Terms used in the description herein are provided only to effectively describe specific embodiments, and are not intended to limit the present disclosure.

Production Example

To provide a positive (or protruding) pattern of the microstructure, a mold with a negative (or concave) pattern is produced using photocurable resin (high temp resin, Formlabs) using a three-dimensional (3D) printer (Form3, Formlabs, USA). Platinum (Pt) may then be deposited on a mold surface where the negative pattern is formed using ion plasma equipment.

Here, density of the negative pattern may be varied by adjusting the separation distance between the microstructures each having a hemispherical structure with a diameter of 1000 μm and a height of 500 μm.

In detail, the mold having a pattern of 4:1 (high density), 2:1, 1:1, and 1:2 (low density) based on the diameter of the structure to the separation distance may be produced.

Inventive Example 1

An electrode of the microstructure may be produced by spraying a silver nanowire (0.32 wt %, in ethanol, Novarials, USA) on the mold surface with a negative pattern density of 4:1 by using a spray gun, and then heat treating the same at 90° C. for 30 minutes.

An intermediate structure may then be produced by spin-coating liquid polydimethylsiloxane (PDMS, 10:1, Sylgard 184, Dow Corning, USA) on the electrode of the microstructure produced above, and then heat treating and curing the same at 160° C. for one hour.

Next, a u-electrode structure including an electrode embedded in PDMS may be produced by removing the produced intermediate structure from the mold in deionized water, and then spin-coating liquid PDMS on the positive microstructure (or pattern) included in the intermediate structure. FIG. 1 schematically shows a series of processes of producing the u-electrode structure.

For producing the pressure sensor having a paired electrode structure, flat-structured ITO/PET (60 ohm/sq, Sigma Aldrich, USA) may be applied as a counter electrode paired with the previously formed u-electrode structure, and for triboelectric induction by its contact with PDMS, perfluoroalkoxy (PFA, Alphaflon, Korea) may be attached (PFA/ITO/PET) to an ITO electrode using carbon tape with double-sided adhesiveness.

Next, the self-powered pressure sensor may be evaluated by attaching the u-electrode structure to a glass substrate, and then fixing a rear surface of the glass substrate that is positioned to be opposite to its surface to which the u-electrode structure is attached to an actuator tip of a universal pressure sensor measurement (UMPS, Teraleader, Korea), and in order to implement a u-triboelectric nanogenerator (TENG) to be used as the pressure sensor, the u-electrode structure and the PFA/ITO/PET positioned to be opposite thereto may be integrated with each other by using a 3M bio tape.

Inventive Example 2

Inventive Example 2 is prepared in the same way as Inventive Example 1, except for the use of the mold produced with the negative pattern having the density of 2:1.

Inventive Example 3

Inventive Example 3 is prepared in the same way as Inventive Example 1, except for the use of the mold produced with the negative pattern having the density of 1:1.

Inventive Example 4

Inventive Example 4 is prepared in the same way as Inventive Example 1, except for the use of the mold produced with the negative pattern having the density of 1:2.

Comparative Examples 1 to 4

Comparative Examples 1 to 4 are performed in the same way as Inventive Example 1, except for the fact that the flat-structured electrode (f-electrode) is produced by performing oxygen plasma treatment of a rear surface of the PDMS intermediate structure including the positive microstructure (pattern) produced without spraying the silver nanowire on the mold surface, that is, its surface positioned to be opposite to the surface on which the positive pattern is formed, spraying the silver nanowire on the rear surface of the intermediate structure on which the oxygen plasma treatment is performed, and then spin-coating the liquid PDMS.

Next, in order to implement the same PDMS surface state as that of the u-electrode structure of Inventive Example 1, Comparative Examples 1 to 4 are performed in the same way as Inventive Example 1, thus implementing an f-triboelectric nanogenerator (f-TENG) including the f-electrode, except for the fact that the liquid PDMS is additionally spin-coated on the surface where the positive pattern is formed.

In addition, Comparative Examples 2 to 4 are performed in the same way as Comparative Example 1, except for the fact that the self-powered pressure sensors are respectively produced to include the PDMS intermediate structure produced using the mold produced with the negative pattern density of 2:1 (Comparative Example 2), the PDMS intermediate structure produced using the mold produced with the negative pattern density of 1:1 (Comparative Example 3), and the PDMS intermediate structure produced using the mold produced with the negative pattern density of 1:2 (Comparative Example 4).

Comparative Example 5

Comparative Example 5 is performed in the same way as Comparative Example 1, except for the fact that an exposed electrode structure is produced by pouring the liquid PDMS into the mold produced based on a production example, curing the same to produce the positive microstructure (pattern), and then applying the silver nanowire on the produced positive structure by using the spray gun.

Experimental Example 1

Analysis on Mechanical and Triboelectric Features
of Triboelectric Nanogenerator System Having
Dual-Electrode Structure FIG. 2 shows the schematic view and scanning electron microscope (SEM) image of the self-powered pressure sensor in Inventive Example 1.

Referring to FIG. 2, it may be seen that the silver nanowire (AgNW) electrode having a thickness of 1 μm is conformally positioned on the outer surface of the PDMS positive microstructure. In addition, a thickness of the outermost PDMS layer is confirmed to be 4.42±1.1 μm.

Next, an analysis may be performed on the mechanical and triboelectric features of the triboelectric nanogenerator (TENG) system which includes, as the second electrode, the dual-electrode structure that includes the u-electrode structure and the f-electrode structure respectively paired with the flat-shaped first electrode (ITO).

First, FIG. 3 shows an operation mechanism of a u-triboelectric nanogenerator (u-TENG) system having the dual-electrode structure that includes the u-electrode structure as the second electrode.

Referring to FIG. 3, in an initial state <i> before a first triboelectrification unit (PFA) and a second triboelectrification unit (PDMS) come into contact with each other, the two triboelectrification units may be in sufficient contact with each other <ii> by an applied external force such as the pressure. In this case, each triboelectrification unit may be charged with the complementary charge. When the applied pressure is decreased and the u-electrode structure is thus moved upward, each surface of the triboelectrification unit that is charged may induce an opposite charge to be formed on the first and second electrodes, thus causing a current flow from the second electrode to the lower first electrode <iii>. The charge on each surface may reach an equilibrium state <iv>, and pressing the u-TENG closer may thus cause the current flow in an opposite direction to that of the current flow <v>.

In this way, reversible charge transfer may be formed by the applied pressure between the first electrode and the second electrode. The u-TENG system resulting from the geometric asymmetry of the two electrodes may not form a capacitor perfectly parallel in the initial state. The contact area between the first triboelectrification unit and the second triboelectrification unit may be increased due to the applied pressure, thus increasing a parallel capacitive intersection region.

FIG. 4 is a view schematically showing a change when the pressure is applied to the u-TENG system and an f-TENG system having the dual-electrode structure that includes the flat structure electrode (f-electrode) as the second electrode.

Unlike the u-TENG system, the f-TENG system having the dual-electrode structure that includes the f-electrode structure as the second electrode, may have the first and second electrodes geometrically symmetric to each other. Accordingly, it may be seen that the parallel capacitive intersection region remains constant, and the pressure-based triboelectric output value depends only on a change in an effective gap distance which is changed based on the elastic modulus of a dielectric material.

From this feature, compared to the f-TENG system, the u-TENG system may be expected to have a significantly higher voltage generated by the contact between the first triboelectrification unit and the second triboelectrification unit resulting from the applied pressure, thus also significantly improving the transfer efficiency of the charges.

In order to verify the above-mentioned effect, a comparative analysis is performed on the open circuit voltage and capacitance change amount of each self-powered pressure sensor of Inventive Example 1 and Comparative Example 1 based on the applied pressure.

Here, the open circuit voltage is measured using an electrometer (electrometer 6514, Keithley, USA), and the capacitance change amount is measured using an LCR (inductance (L), capacitance (C), and resistance (R)) meter (E4980A, Keithley, USA).

FIGS. 5A, 5B, and 5C are views each showing an open circuit voltage (real-time Voc) reacting in real time, an open circuit voltage, and a hysteresis curve of the open circuit voltage, based on the applied voltage.

Referring to FIGS. 5A and 5B, it may be seen that Inventive Example 1 shows an open circuit voltage feature that is up to three times improved compared to that of Comparative Example 1.

In addition, referring to FIG. 5B, it is confirmed that first pressure sensitivities $S_1$ of Inventive Example 1 and Comparative Example 1 are 1.04 V/kPa and 0.33 V/kPa, respectively, when the applied pressure is 1 kPa or less, and second pressure sensitivities $S_2$ of Inventive Example 1 and Comparative Example 1 are 0.19 V/kPa and 0.08 V/kPa, respectively, when the applied pressure is more than 1 kPa. It is also confirmed that Inventive Example 1 has the pressure sensitivity significantly superior to that of Comparative Example 1.

FIG. 6 is a view showing the capacitance change amount based on an applied pressure. As shown in FIG. 6, it may be seen that Inventive Example 1 has the capacitance change amount significantly improved compared to that of Comparative Example 1, and it is observed that this result is more noticeable than the improvement in the open circuit voltage feature described above. This feature may result from a surface potential difference caused by the PDMS positioned on the positive pattern surface, that is, positioned on the outer surface of the electrode in the u-electrode structure including the electrodes embedded in the PDMS.

In addition, the capacitance change amount based on density of the positive pattern included in each electrode structure is measured.

FIG. 7 is a view showing each capacitance change amount measured when applying a pressure of 9.5 kPa compared to capacitance before applying the pressure for Examples 1 to 4 and Comparative Examples 1 to 4.

Referring to FIG. 7, it is observed that the capacitance change amount of the u-TENG system is decreased as the density of the positive pattern is decreased. On the other hand, it is observed that the capacitance change amount of the f-TENG system is increased as the density of the positive pattern is decreased.

The reason is that in the case of the u-TENG system, the self-powered pressure sensor including a high-density positive pattern may have an increased overall parallel capacitive intersection region as the pressure is applied thereto. However, in the case of the f-TENG system, the change in the effective gap distance depending on the elastic modulus of the dielectric material is maximized in the self-powered pressure sensor including a low-density positive pattern, as described above. However, it may be seen that there is still a significant difference in an absolute value of the capacitance change amount.

Furthermore, comparison and analysis are additionally performed on the triboelectric features based on the shape of the microstructure forming the pattern.

FIG. 8A is a view schematically showing the shape of the microstructure, and FIGS. 8B and 8C are views respectively showing the change in the contact area and a strain-stress curve based on the pressure acquired through simulation of the structure including the positive pattern having the shape of each microstructure.

Here, the shape of the microstructure uses the hemisphere shape or the truncated cone shape, each having a diameter of 1000 μm, and the diameters of their cut parts in contact with the PFA layer are set to 100 μm, 140 μm, 300 μm, 600 μm, and 1000 μm, and respectively named as Cone 100, Cone 140, Cone 300, Cone 600, and Cone 1000. Here, the microstructures are respectively set to have the same height of 500 μm.

In addition, in the structure including the positive pattern that additionally has the shape of each microstructure, the density of the positive pattern is adjusted by the ratio of the microstructure diameter to the separation distance as described above to also compare and analyze the effect of the positive pattern on the density, and the simulations are performed using COMSOL multiphysics software (ver 5.6. COMSOL Inc., USA).

Referring to FIG. 8B, which shows the change in the contact area based on the pressure, it may be seen that the hemisphere shape shows the largest change in the contact area based on the pressure when including the positive pattern having the ratio of the microstructure diameter to the separation distance of 2 to 1, and it is confirmed that the truncated cone shape shows a smaller change in the contact area as its cut part has a larger diameter.

For sensitivities of the hemisphere shape, Cone 100, and Cone 600 based on the pressure, a contact area change value acquired through the simulation is compared and analyzed with an actually measured open circuit voltage measurement value.

FIGS. 9A and 9B are views respectively comparing the change in the contact area based on the pressure acquired through the simulation and the open circuit voltage based on the pressure acquired through the measurement.

Referring to FIGS. 9A and 9B, it is confirmed that each of the hemisphere shape and Cone 100 shows a simulation result value and an actual measurement result value which are consistent with each other. In particular, it is confirmed that the hemisphere shape has the best pressure sensitivity of 2.14 V/kPa when used as the microstructure and including the positive pattern having the ratio of the microstructure diameter to the separation distance of 4:1.

On the other hand, it may be seen that Cone 600 shows the simulation result value and the actual measurement result value which are different each other, which is determined to be caused by non-ideal contact between the PFA surface and Cone 600 in the initial state. That is, the result value may depend on a surface roughness of the cut part as the cut part in contact with the PFA surface has the larger diameter, which may decrease the reliability of the pressure sensor because the non-ideal contact caused by the surface roughness may not be easily controlled.

Experimental Example 2

Comparison and Analysis of Reliability and Durability of Self-Powered Pressure Sensors The reliability of the self-powered pressure sensor is analyzed based on its reproducibility and reversibility, and the mechanical durability of the self-powered pressure sensor is analyzed based on its long-term stability based on a pressure loading/unloading cycle.

FIG. 10A, FIG. 10B, FIG. 10C and FIG. 10D are views respectively showing reproducibility results of five different samples each produced according to Example 1, a measurement result of the open circuit voltage measured in real time based on pressure levels from 0.06 to 10.1 kPa, hysteresis curves respectively acquired by setting pressures of 0.8 to 20 kPa as the maximum loading pressure, and a result of long-term stability test for 10,000 cycles by using one cycle of loading/unloading a pressure of 10 kPa.

Referring to FIG. 10A, it may be seen that all the five different samples produced according to Inventive Example 1 show almost similar features, which confirms that these samples have remarkably excellent reproducibility.

In addition, as shown in FIGS. 10B and 10C, it is confirmed that the self-powered pressure sensor has excellent reversibility and hysteresis feature.

Furthermore, as shown in FIG. 10D, it is confirmed that the sensor shows a repetitive and stable load voltage feature (−0.3 to 0.3V) as a result of performing the long-term stability test for 10,000 cycles by using one cycle of loading/ unloading the pressure of 10 kPa.

On the other hand, even though not shown in the drawings, as a result of performing the long-term stability test of the pressure sensor produced according to Comparative Example 5, it is confirmed that its load voltage appears unstable within 500 cycles, which confirms the decreased mechanical durability.

Experimental Example 3

Performance Test of Self-Powered Pressure Sensor

Performance of the self-powered pressure sensor described above is evaluated using this sensor as the sensor for pulse and acoustic pressure detection.

FIG. 11 is a view showing sensing sensitivity of the sensor when the self-powered pressure sensor produced according to Example 1 or Comparative Example 1 is applied for the pulse detection.

Here, each sensor is attached to the wrist of a woman (volunteer 1) and the wrist of a man (volunteer 2), and the voltage output is monitored in real time.

As shown in FIG. 11, Comparative Example 1 shows few discernible pulse waves when comparing a triboelectric signal of a wrist pulse pressure measured in his/her rest state. On the other hand, it is confirmed that Inventive Example 1 may detect clear peaks distinguished as 1 (contraction peak), 2 (crossing point), and 3 (relaxation peak), and it may be seen that Inventive Example 1 may detect a, b, and c, which represent anti-triboelectric signals respectively corresponding to 1, 2, and 3.

In addition, it is confirmed that Inventive Example 1 may detect an increased pulse rate after physical activity (e.g., performing squats for less than 1 minute) with the excellent reliability and stability.

Next, detection performance of the acoustic pressure having various frequencies is evaluated using the self-powered pressure sensor of Inventive Example 1.

FIG. 12A is a view showing an experimental setup for evaluating the detection performance of the acoustic pressure, FIG. 12B is a view showing the voltage output based on a pressure of the acoustic pressure at a frequency of 500 Hz, and FIGS. 12C to FIG. 12H are views respectively showing temporal response results of the pressure sensor at frequencies of 0.1 kHz, 0.5 kHz, 1 kHz, 2 kHz, 4 kHz, and 10 kHz.

As shown in FIG. 12A, in order to evaluate the detection performance of the acoustic pressure having the various frequencies, the self-powered pressure sensor, a speaker (BR-1600BT, Britz, Korea) and a digital sound level meter (SPL, SL-4101, Lutron Electronic, USA) produced according to Inventive Example 1 are disposed in a soundproof box.

Here, the speaker and the self-powered pressure sensor may be disposed to be spaced apart by 5 cm from each other.

Referring to FIG. 12B, it may be seen that the self-powered pressure sensor has sensitivity of 1.02±0.28 mV/Pa at 500 Hz, and that the acoustic pressure and the voltage output show a linear relationship.

In addition, referring to FIGS. 12C to 12H, it is confirmed that the self-powered pressure sensor shows a reliable response at each frequency when receiving a sinusoidal acoustic wave by using a function generator.

In addition, detection performances of music and voice are evaluated using the self-powered pressure sensor of Inventive Example 1.

FIG. 13 is a view comparing waveforms of actual sound sources for music and voice with waveforms of sound sources for music and voice recorded using the self-powered pressure sensor.

Here, the actual sound source for the voice is recorded using a smartphone.

As shown in FIG. 13, it is confirmed that the waveform of the actual sound source and the waveform recorded using the self-powered pressure sensor appears very similar to each other.

From this fact, it may be seen that the self-powered pressure sensor according to an embodiment of the present disclosure shows very excellent quality features in the acoustic pressure detection.

As set forth above, the self-powered pressure sensor according to the present disclosure may include: the first electrode; the first triboelectrification unit positioned on the first electrode; the second triboelectrification unit including the pattern on which the microstructure is repeatedly positioned, the microstructure being reversibly in contact with or separated from the first triboelectrification unit by the physical external force, and having at least one surface in contact with the first triboelectrification unit to induce the change in the contact area; and the second electrode positioned inside the second triboelectrification unit and conformally positioned on the surface of the microstructure, wherein the first electrode and the second electrode are geometrically asymmetric to each other. Therefore, the sensor may show the excellent pressure sensitivity when the pressure is applied thereto by improving the capacitance change rate due to the increased parallel electric field region induced by the change in the contact area of the second triboelectrification unit, and significantly improving the transfer efficiency of the charges generated by the triboelectrification simultaneously.

Hereinabove, the present disclosure has been described by the specific matters and embodiments, which have been provided only for assisting in comprehensive understanding of the present disclosure. Therefore, the present disclosure is not limited to the embodiments, and various modifications and changes may be made by those skilled in the art to which the present disclosure pertains from this description.

Therefore, the spirit of the present disclosure should not be limited to these embodiments, and the claims and all of modifications equal or equivalent to the claims are intended to fall within the scope and spirit of the present disclosure.

What is claimed is:

1. A self-powered pressure sensor comprising:
a first electrode;
a first triboelectrification unit positioned on the first electrode;
a second triboelectrification unit comprising a microstructure pattern including a plurality of microstructures, each microstructure being reversibly in contact with or separated from the first triboelectrification unit by a physical external force, and having at least one surface in contact with the first triboelectrification unit to induce a change in a contact area; and
a second electrode positioned inside the second triboelectrification unit, the second electrode comprising an electrode layer positioned on a surface of the microstructure and having a structure parallel to the surface of the microstructure,
wherein the first electrode and the second electrode are geometrically asymmetric to each other.

2. The sensor of claim 1, wherein the microstructure has any one selected from the group consisting of sphere, hemisphere, cone, truncated cone, polygonal pyramid, and truncated polygonal pyramid shapes.

3. The sensor of claim 2, wherein the microstructure has the hemisphere or the truncated cone shape.

4. The sensor of claim 3, wherein the microstructure has the hemisphere shape.

5. The sensor of claim 4, wherein a microstructure diameter is 200 to 2000 μm and a microstructure height is 100 to 3000 μm.

6. The sensor of claim 1, wherein the first electrode has a flat structure.

7. The sensor of claim 1, wherein the first triboelectrification unit and the second triboelectrification unit include different materials.

8. The sensor of claim 1, wherein the first triboelectrification unit includes any one selected from the group consisting of fluorinated ethylene-propylene copolymer (FEP), polyvinylidene fluoride (PVDF), perfluoroalkoxy alkane (PFA), and ethylene-tetrafluoroethylene copolymer (ETEF).

9. The sensor of claim 1, wherein the second triboelectrification unit includes a siloxane-based polymer.

10. The sensor of claim 1, wherein the second electrode includes a metal nanowire.

11. The sensor of claim 1, wherein a separation distance between the surface of the microstructure and the second electrode is 1 to 30 μm.

12. The sensor of claim 11, wherein a thickness of the second electrode is 0.5 to 2 μm.

13. The sensor of claim 12, wherein a ratio of the thickness of the second electrode to the separation distance between the surface of the microstructure and the second electrode is 1:1 to 30.

14. The sensor of claim 1, wherein elastic modulus of the first triboelectrification unit is $10^2$ times or more than that of the second triboelectrification unit.

15. The sensor of claim 1, wherein the microstructure is repeatedly positioned on the pattern for a ratio of a microstructure diameter to a separation distance between the closest microstructures to be 1:0.25 to 2.

16. The sensor of claim 1, wherein the self-powered pressure sensor has pressure sensitivity of 0.1 to 5 V/kPa when a pressure is applied thereto.

* * * * *